US 6,555,389 B1

(12) United States Patent
Ullman et al.

(10) Patent No.: US 6,555,389 B1
(45) Date of Patent: Apr. 29, 2003

(54) SAMPLE EVAPORATIVE CONTROL

(75) Inventors: Edwin F. Ullman, Atherton, CA (US); Sharat Singh, San Jose, CA (US); Ian Gibbons, Portola Valley, CA (US); Travis Boone, Oakland, CA (US); Torlief Bjornson, Gilroy, CA (US)

(73) Assignee: Aclara BioSciences, Inc., Mountain View, CA (US)

( * ) Notice: Subject to any disclaimer, the term of this patent is extended or adjusted under 35 U.S.C. 154(b) by 0 days.

(21) Appl. No.: 09/470,677

(22) Filed: Dec. 23, 1999

Related U.S. Application Data
(60) Provisional application No. 60/133,448, filed on May 11, 1999, and provisional application No. 60/140,180, filed on Jun. 18, 1999.

(51) Int. Cl.[7] ............................................. G01N 33/558
(52) U.S. Cl. ......................... 436/514; 422/55; 422/58; 422/68.1; 422/82.01; 422/101; 435/287.1; 435/288.4; 435/288.5; 436/149; 436/150; 436/151; 436/518; 436/535
(58) Field of Search ..................... 422/55, 58, 68.1, 422/82.01, 101; 435/287.1, 288.4, 288.5; 436/514, 518, 535, 149, 150, 151

(56) References Cited

U.S. PATENT DOCUMENTS

| | | | |
|---|---|---|---|
| 5,126,022 A | 6/1992 | Soane et al. | 204/180.1 |
| 5,282,543 A | 2/1994 | Picozza et al. | 220/255 |
| 5,304,487 A * | 4/1994 | Wilding et al. | 435/291 |
| 5,576,197 A | 11/1996 | Arnold | 435/91.2 |
| 5,599,432 A | 2/1997 | Manz et al. | 204/451 |
| 5,750,015 A | 5/1998 | Soane et al. | 204/454 |
| 5,842,787 A * | 12/1998 | Kopf-Sill et al. | 366/340 |
| 5,858,195 A | 1/1999 | Ramsey | 204/601 |
| 5,885,470 A | 3/1999 | Parce et al. | 216/33 |
| 5,976,336 A * | 11/1999 | Dubrow et al. | 204/453 |
| 6,156,181 A * | 12/2000 | Parce et al. | 204/600 |
| 6,186,660 B1 * | 2/2001 | Kopf-Sill et al. | 366/340 |
| 6,235,175 B1 * | 5/2001 | Dubrow et al. | 204/453 |

FOREIGN PATENT DOCUMENTS

| | | |
|---|---|---|
| WO | WO 98/33052 | 7/1998 |
| WO | WO 99/34920 | 7/1999 |
| WO | WO 00/25921 | 5/2000 |

* cited by examiner

Primary Examiner—Christopher L. Chin
(74) Attorney, Agent, or Firm—Peter J. Dehlinger; Perkins Coie, LLP

(57) ABSTRACT

Devices and methods are provided using microfluidic devices for manipulating small volumes and determining a variety of chemical and physical events. The devices rely upon an opening to the atmosphere of a small volume in a zone, where a sample is placed in the zone where evaporation can occur. The zone is maintained in contact with a liquid medium that serves to replenish the liquid in the zone and maintain the composition of the mixture in the zone substantially constant. The diffusion of components in the zone is restricted during the course of the determination by the liquid flux into the zone.

6 Claims, 8 Drawing Sheets

SAMPLE EVAPORATIVE CONTROL

CROSS-REFERENCE TO RELATED APPLICATIONS

This application is a continuation-in-part of provisional applications 60/133,448, filed on May 11, 1999 and 60/140,180, filed Jun. 18, 1999, which disclosures are incorporated herein by reference.

INTRODUCTION

1. Technical Field

The field of this invention is manipulation of small volumes comprising a volatile liquid.

2. Background

Microfluidic devices comprise small capillary channels in a solid substrate, where the channels are usually present as a network. Various orifices are provided for communicating with the channels. Because of the small volumes of the networks and the individual channels many benefits adhere. The small volumes require less reagent and sample, frequently being limited by the level of detection available. In addition, because of the small volumes, reactions are very rapid. The networks allow for efficient movement of the components from one site to the next and with little loss of the components. Also, various components may be brought together, separated by different operations and the individual fractions used for various purposes.

The microfluidic devices lend themselves for various assays involving candidate compounds, where binding events are measured, enzyme activity measured, or metabolic processes measured. In this way, the effect of the candidate compounds on the indicated events may be determined. Where one is interested in comparing the effect of different candidate compounds, it is necessary that the amount of the candidate compound and other components, which affect the measured outcome, be reasonably known. For the most part, solutions that will be used are aqueous. Unless one uses relatively drastic measures, the water will rapidly evaporate. Transfers of aqueous or other solutions involving manipulative steps where the solution is exposed to the atmosphere for any length of time will invariably result in some evaporation, particularly where there are sequential additions, and the solvent from the earlier additions is evaporating while adding the next addition and during the interim between additions. In addition, incubations can result in evaporation, even where the container is covered. The problem is exacerbated where one is interested in high throughput screening, which may involve many very small aliquots of different solutions to multiple sites on a microfluidic device. Using foreign substances to diminish the evaporation can lead to contamination, require repetitive cleaning and create other detrimental issues.

Various methods have been tried, such as cooling the liquids, so as to substantially reduce evaporation, adding a lower volatility liquid over the surface of the sample, ambient humidity, adding droplets of solvent to the sample after its deposition to maintain the volume, and the like. All of these approaches are not generally useful and have severe disadvantages for use with small volumes, which must be transferred to a reaction vessel. There is a need for improved methods for manipulating nanoliter volumes when dealing with microfluidic devices, particularly associated with high throughput screening of compounds, diagnostic assays or other investigative procedures.

3. Brief Description of the Prior Art

U.S. Pat. Nos. 5,576,197 and 5,282,543 disclose the use of wax and other flexible materials, respectively, to inhibit evaporation. Microfluidic devices are described in U.S. Pat. Nos. 5,885,470; 5,858,195; 5,750,015; 5,599,432; and 5,126,022. Methods of evaporative control are disclosed in WO98/33052 and WO99/34920.

SUMMARY OF THE INVENTION

Methods and devices are provided for the manipulation of small volumes in association with determinations employing microfluidic devices, where a substantial portion of the liquid is subject to evaporation during the operation. The microfluidic devices compromise a partial enclosure for a zone for receiving a small amount of solute, usually as a solution, comprising a component of a reaction. The zone has a non-wettable border. During the transfer to the zone, the liquid in the zone is subject to evaporative loss of liquid, and the zone is in fluid exchange relationship with a channel housing a solution. The channel solution replenishes the liquid in the zone and may serve as a source of a second or more components of the reaction. Either substantially immediately upon entering the zone, the solute is in contact with the channel solution, so that any solvent lost by evaporation can be replenished or evaporation of any solvent occurs and the residue is dissolved in a solvent discharged from a capillary channel, where contact is maintained with the solution in the zone and the solution in the capillary channel. The reaction volume is substantially maintained in the zone defined by a major portion of the components of interest being present in the zone, usually involving the region between a meniscus and the region of fluid exchange between the zone and the channel.

BRIEF DESCRIPTION OF THE FIGURES

FIGS. 2A-1, 2B-1 and 2C-1 are diagrammatic cross-sectional views of units of a subject microfluidic device, having two channels and a central chamber, at various stages in the process of using the device;

DESCRIPTION OF THE SPECIFIC EMBODIMENTS

Figure 1:
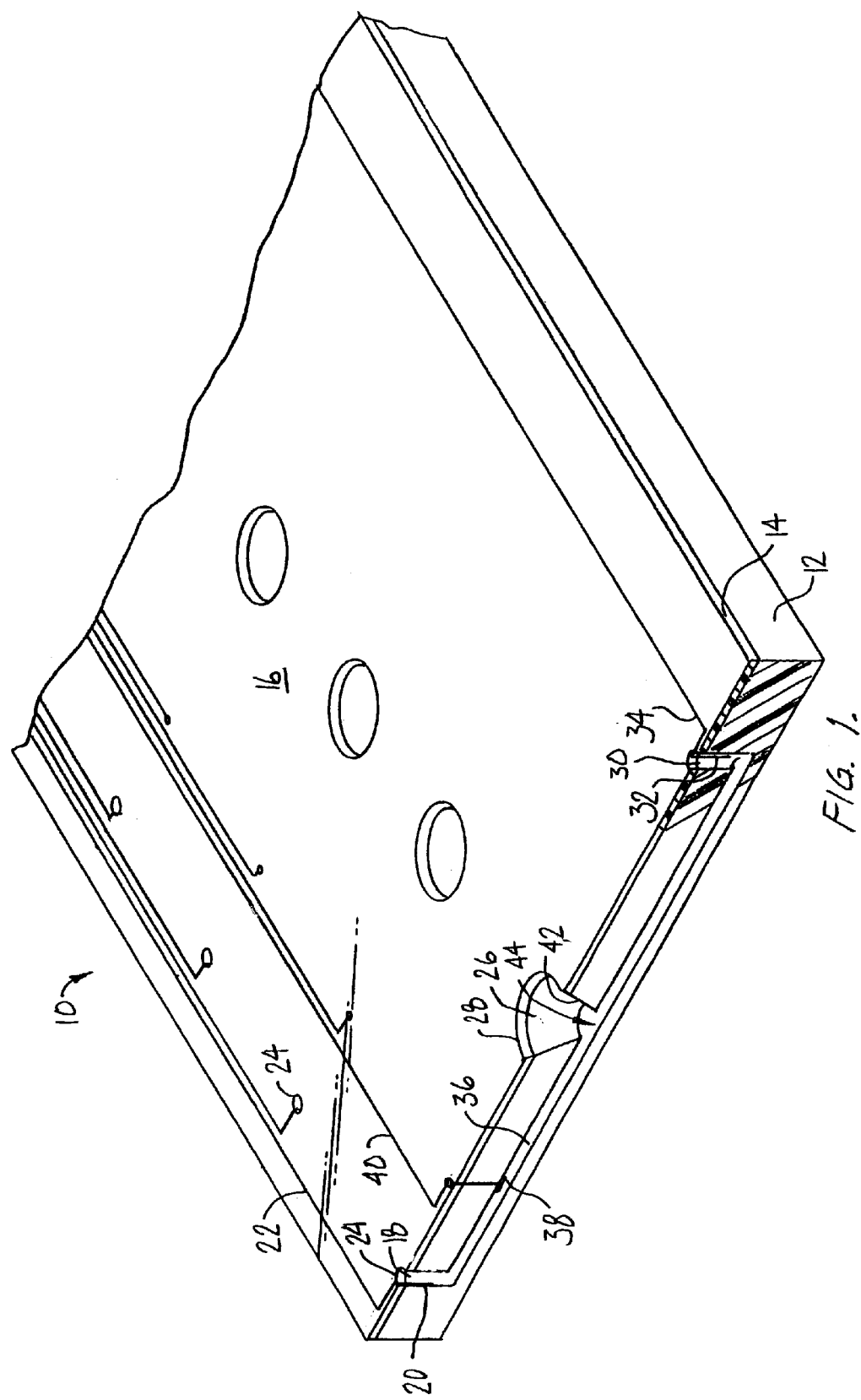
FIG. 1 is a fragmentary perspective view of a microfluidic device according to this invention.

Improvements are provided for performing reactions in microfluidic devices, using methods and devices allowing for efficient manipulation of small volumes of solutions comprising evaporative solvents. The reaction components will normally be in one or more additions to the zone and optionally a liquid in a channel in liquid exchange relationship with the zone. The channel liquid may one or more components, or all of the components of the reaction may be added to the zone. Microfluidic devices are provided comprising at least one unit having a partial enclosure defining a portion of the zone and connected to a capillary channel, so as to be open to the atmosphere during additions to the zone, which enclosure may be sealed after each manipulation or after all manipulations are complete. The liquid containing capillary channel is in liquid transfer relationship with the zone, replenishing liquid lost by evaporation and creating a liquid flux in the channel toward the zone. The opening permits convenient addition of solutes and solutions to the zone, where evaporation of liquid into the atmosphere may occur during the transfer of the solution into the zone and thereafter. The conditions of the addition will usually be at ambient or elevated temperature and pressure, although higher temperatures may be employed during the addition. The zone has a non-wettable border. Because of the non-wettable border, the height of the meniscus which forms at the region between the wettable and non-wettable borders will be restored to its equilibrium level, due to evaporation and fluid movement into the capillary channel. The method permits the formation of the product of the reaction to be retained within a small volume for ease of detection.

Assays may be carried out for extended times with nanovolume reaction mixtures comprising a volatile solvent, while the reaction mixture is exposed to the atmosphere. Reaction volumes of 50 to 500 nl are employed, where one or more components are added to the reaction zone containing the reaction volume, where the components or their products are substantially retained in the zone. The components are added as solutions of from about 10 to 300 nl, more usually of from about 10 to 200 nl, and preferably not more than about 100 nl. The reaction mixture is bounded by a meniscus bordered by an interface between a wettable and non-wettable boundary (hydrophilic and hydrophobic boundary) and the solution directly under the meniscus. The additions are made directly onto or through the meniscus, which may be surrounded by a wall forming a passageway. Of particular interest are binding assays involving proteins, where a candidate compound is tested and the binding level of the candidate compound to the protein is determined. The assay protocol involves a reaction mixture having a meniscus exposed to the air, where the candidate compound may be in the liquid of the reaction mixture with the meniscus cover or added to the reaction mixture. At least one other component of the reaction is then added to the reaction mixture, in accordance with the requirements of the determination, e.g. substrate for an enzyme, competitive labeled compound for a binding protein, etc. Depending on the nature of the label and the protocol, the label may be detected in the reaction mixture.

The zone is defined functionally as comprising at least about 50% of a component of interest, usually at least about 50% of the components added to the zone, preferably at least 60%, more preferably, at least about 80% and up to 95 or 100%. The zone will always be a very small volume and where the operation of interest provides a detectable signal, will usually be the region from which the signal is detected. Desirably, the zone will be easily addressable to maximize the signal for the determination, so that the zone may approximate a cylinder. Generally, the zone will be under 5 $\mu$l, more usually not greater than about 500 nl and may be 100 nl or less. Therefore, the major portion of the signal will be contained in the zone. As will be described, the zone need not be significantly enclosed and may be confined by solid and liquid barriers, in addition to being open to the atmosphere, at least initially during the operation.

The zone will have a portion of the zone at a non-wettable/wettable interface or border. (By wettable is intended that the surface will be coated with the liquid and in a capillary the liquid will move through the capillary by surface tension. In the case of a polar solvent, particularly an aqueous solvent, the surface will be hydrophilic, while the non-wettable surface will be hydrophobic. Where the solvent is non-polar, e.g. hydrocarbon, the reverse will be true for wettable and non-wettable.) This interface may be at a region in an enclosure, at the edge of a capillary, where the outer portion of the capillary is non-wettable, or other structure where migration of the liquid in the zone is inhibited from moving into another area as a result of the surface tension or contact angle between the liquid and the non-wettable area.

In referring to microfluidic devices it is intended that the devices comprise capillary channels having cross-sections of less than about 5 mm$^2$, usually less than about 1 mm$^2$, more frequently less than about 0.1 m$^2$, and frequently as small as about 0.005 mm$^2$ or less, generally be at least about 0.025 mm$^2$, more usually at least about 0.01 mm$^2$. In addition, the devices have a zone in which the reaction of interest occurs, which when partially enclosed, so that a volume can be defined, the volume of the zone that comprises the liquid of interest will be less than about 5 $\mu$l, usually less than about 1 $\mu$l, and frequently less than about 0.5 $\mu$l, and may be as small as about 50 nl or less, usually at least about 10 nl. The reaction volume will normally be bordered by a meniscus at the non-wettable border and will include the volume above the non-wettable border and may also include a volume in the capillary channel continuous with the volume extending beyond the plane defined by the non-wettable border. The partial enclosure, when present, may have a substantially larger volume than the volume of the zone, usually not more than about 10× larger, more usually not more than about 5× larger, than the volume of the zone.

The capillary channel may be round, rectangular, frusto-conical, truncated pyramid, normally inverted, or other shape, preferably a regular shape. Of particular interest is when the capillary channel is formed in a substrate, e.g. a plastic card, and the channel is enclosed with a film which is adhered to the body of the substrate. In this case, the channel will not be circular and will have a depth and width. In addition, the width and/or depth may not be constant the length of the channel. In referring to width and/or depth, it is intended the average width, although differences from the average will not exceed more than by 100%, usually by not more than about 50%.

For the non-circular channel, the depth of the capillary channel will generally be in the range of about 10 $\mu$m to 2 mm, usually in the range of about 25 $\mu$m to 1 mm, more usually in the range of about 25 $\mu$m to 500 $\mu$m, preferably less than about 250 $\mu$m, and at least about 10 $\mu$m, usually at least about 20 $\mu$m, particularly where the capillary channel serves as the floor of the zone. For the circular capillary, the diameter will generally be in the range of about 10 $\mu$m to about 2 mm, more usually at least about 20 $\mu$m to 2 mm. While the device may have one or more capillary channels in liquid exchange relationship with the zone, the channels may be in the same or different plane, so that there may be liquid contact at two or more different interfaces.

Conveniently, the signal may be determined without having to view the signal through the material with which the device is composed.

By having a network of channels, where some or all of the channels may interconnect, substantial flexibility is achieved. It is understood that for the purposes of this invention, channels and capillaries may be used interchangeably, where capillary intends that there is liquid movement upon introduction of liquid into one end of a channel due to surface tension. The channels may serve to deliver and remove agents from one or more zones, simultaneously or successively, depending on the plumbing employed. One may provide for miniaturized pumps, separation walls, gates, etc., so as to be able to direct liquids to specific zones. One may provide for successive replacement of liquids in the channels, whereby different reagents may be directed to the zones, which allows for modification of reactions, stepwise performance of reactions, removal of agents from the zones, etc. By modulating the temperature of the liquid in the channels one can modulate the temperature of the liquid in the zone. Thus, one could provide for heating and cooling of the mixture in the zone.

The zones provide opportunities for the introduction of one or a few particles, such as beads, colloidal particles, cells, organelles, microsomes, and the like. The small volumes allow for enhanced signals from the particles, allowing for investigations or determinations, where only a few particles need be present. For cells, one may provide 1 cell or more, usually more than about 50 cells for statistically significant results, and generally fewer than 1,000 cells, usually fewer than about 500 cells. Cells may be dispersed in the zone, adhered to the surface of the zone, as a wall of a chamber, or the like.

In one embodiment, one has an orifice through the wall of a capillary channel, where the partial enclosure is at least the height of the thickness of the wall of the capillary. In this embodiment, where the wall is non-circular, the orifice is normally in the cover enclosing the channel in the substrate. The orifice can be varied in accordance with the thickness of the cover, which up to a degree may be arbitrarily chosen. Thus, covers may be from about 0.05 to 2 mm in thickness, where the height of the orifice would be the same. Alternatively, one may fuse or form a tube or collar to the substrate to obtain any length for the partial enclosure. The partial enclosure serves as a container, generally having a cross-sectional area at least about one-quarter, frequently at least about one-half and desirably at least about the same cross-sectional dimension of the channel or a larger dimension. The volume of liquid in the zone will be controlled in part by the nature of the wall of the partial enclosure of the zone, where at least a portion of the wall will be non-wettable by the liquid in the zone. (By "non-wettable" is intended that the liquid in the zone will not migrate past the region that is non-wettable when no force is applied to the liquid to drive the liquid past such region. In effect, the contact angle between the liquid and the wall is such as to inhibit the rise of the liquid in the partial enclosure. Conversely, "wettable" intends that the liquid will wet the surface and rise in a capillary in the absence of a negative force.)

For the most part, the liquid in the zone will be aqueous (hydrophilic) and a demarcation for the height of the liquid in the zone will be created by having a non-wettable border or wall. Thus, the reaction zone will be the liquid from the interface between the channel and the meniscus that forms as result of the non-wettable region of the wall of the enclosure and may also include the region in the channel below the meniscus. For a hydrophilic liquid and a non-wettable wall, the meniscus will be convex.

In this embodiment it appears that the evaporation from the zones results in the movement of liquid from the channel into the zone to retain the height of the meniscus. The liquid in the channel is, of course, maintained by the reservoir(s), whose volume will generally be large compared to the volume of the channel and the liquid in the zone. As a result of the meniscus in the zone, the evaporation from the zone per unit cross-sectional area of the zone will be greater than the evaporation per unit cross-sectional area of the reservoir. The difference may be further enhanced by having: a temperature differential between the liquid in the zone and the liquid in the reservoir; a differential air flow; a differential humidity; or the like, where the condition at the zone is to enhance the evaporation per unit area at the zone, as compared to the reservoir. The temperature during the time of addition may be ambient, reduced or elevated, generally in the range of about 10° C. to about 65° C., more usually in the range of about 20° C. to 50° C., so long as the rate of evaporation is not unduly great to interfere with the replenishment.

In other embodiments, one may have a discontinuity between the liquid in the zone and the liquid in the channel, where liquid from the channel may be brought into contact with liquid in the zone. In this instance, the zone may be substantially open and only have a floor or be substantially enclosed, where the channel could be connected to the zone through an orifice at the bottom or at the side of the zone. One has a channel in proximity to the zone, where the liquid in the channel may be expressed into the zone and optionally withdrawn to reduce, but not completely terminate, evaporation during subsequent operation.

Depending upon the nature of the operation, different protocols may be employed.

In one protocol, a liquid, normally a solution, is added to the zone and upon introduction into the zone comes into substantially immediate contact with liquid from a capillary channel. The liquid may be added to the zone, where the channel liquid may be the floor of the zone, a droplet between two channels or may be in a side channel, where the channel may be vertical or horizontal in relation to the zone. The solution may be retained in the zone or withdrawn into the capillary channel during the course of the reaction. After sufficient time for reaction to occur, the resulting product may be processed in accordance with the operation, and, as appropriate, a signal determined. As an illustration, with a volume of the zone of about 200 nl, with a capillary channel having a cross-sectional area of 450×100 $\mu$m, the zone would be withdrawn into the capillary about 4–5 mm, assuming all of the reaction mixture in the zone was withdrawn into the channel.

In a second protocol, a solute or solution may be added to a surface in the zone and any evaporation of the solvent ignored. (While frequently referring to a solution, since for the most part solutions will be involved, in some instances a pure liquid will be used, rather than a solution or mixture of liquids.) Liquid for the reaction mixture is then discharged from the channel to dissolve the residue, liquid or solid, to form the reaction mixture. The reaction mixture solution is maintained in contact with the liquid in the channel to replenish any solvent, which evaporates, or the reaction solution is withdrawn into the channel to substantially inhibit any evaporation. After sufficient time for reaction to occur, the resulting product may be processed in accordance with the operation, and, as appropriate, a signal determined.

Evaporation helps keep the zone of the reaction mixture defined. Despite the diffusion of small molecules, the liquid flux into the zone during the operation inhibits the loss of the small molecules into the channel away from the zone. Based on this consideration, preferably the zone will be designed to have a relatively short vertical path from the meniscus to the end of the zone. Furthermore, depending on the height of the partial enclosure, one can add various solutions, where the solutions will mix in the partial enclosure and as the height of the meniscus is restored through evaporation and the liquid moving into the channel, the channel liquid is moved back into the channel, rather than the solution of the reaction components.

In performing the reaction there will be at least one component of the reaction added through the opening into the zone and, as described, conveniently, at least one component of the reaction in the solution in the channel. Frequently, components added to the zone will be higher molecular weight components of the reaction, generally exceeding 2 kD, frequently exceeding 5 kD, and may exceed 10 kD. Where small organic molecules are being screened for activity, these will usually be added to the zone and will have a molecular weight in the range of about 150–250 kDal. One or more additions may be made into the zone, adding one or more components to the zone. To minimize the additions, mixtures of components may be added. By virtue of the contact between the solution in the zone (zone solution) and the solution in the channel (channel solution), components in the channel solution will diffuse into the zone solution to equilibrate the concentration of the component(s) in the channel solution between the two solutions, while evaporation keeps the zone defined. Upon completion of the addition(s), one can then determine whether the desired reaction occurred.

A plurality of additions may be made concurrently or consecutively, where the time between additions may be very short, bordering on simultaneous addition, or require relatively long intervals, e.g. 30 sec or more, where the intermediate reaction mixtures may be incubated, processed, e.g. heated, or withdrawn into the channel to inhibit evaporation. Generally, the volume of the solution added to the zone will be less than 0.005 ml, frequently less than about 1 $\mu$l and more frequently less than about 0.5 $\mu$l usually being at least about 1 nl, more usually being at least about 5 nl, frequently at least about 10 nl, depending on the ability to accurately transfer liquids to the zone.

Additions may be achieved using piezoelectric devices, e.g. ink-jet devices, pins, slotted pins, pipettes, capillary electrophoresis injection, etc. The particular manner of transfer will depend on the volume to be transferred, the nature of the composition to be transferred, the speed with which the composition can be transferred, the accuracy required for dispensing the composition, and the like.

Usually, the solution in the channel will be a buffered solution, where the formality of the buffer, which may include other ions, will be not more than about 200 mM, more usually not more than about 100 mM, and frequently less than about 75 mM, usually greater than about 5 mM, more usually being greater than about 10 mM. Buffers which may find use include phosphate, carbonate, borate, MOPS, HEPES, Tris, tricine, etc., the buffer generally being selected in accordance with the nature of the reaction. The concentration of the components, which are added, may vary widely depending on the volume of the solution. Concentrations may vary from about 1 pM to 0.1M, usually being in the range of about 1 nM to 0.01M, the concentration and volume depending on the level of detection of the detectable signal and the manner in which the signal is generated. Since the volumes added to the zone are small compared to the volume of solution in the system comprising the channel and reservoir, the area of interface between the zone and channel is small, and the evaporative flux inhibits diffusion of components of the zone from leaving the zone, there will be limited equilibration between the added solution and the liquid in the channel.

Desirably, the buffer solution in the channel will be the same as the buffer solution in the added solutions, where the difference will then be as to the components and any non-aqueous solvents. One can enhance fluid flow toward the zone by having the added solution at a higher formality than the solution in the channel, although an increased formality of the added solution will occur as a result of evaporation, except for the compensation provided by the solution in the channel. Where a component, particularly the test compound, is added as a non-aqueous solution, it may be desirable to include the test compound in the reservoir and channel, rather than adding the solution to the opening in the zone. This avoids problems of dissolving the test compound in the buffer solution, where the test compound is only moderately soluble in water. In this way, the non-aqueous solvent becomes equilibrated in the reservoir(s) and the test compound is instantaneously diluted into the buffer, preventing separation of the test compound.

The subject device can allow for sample dilution, for example, where the sample comprises a solvent that may interfere with an intended operation. One can add the sample solution to a reservoir prior or subsequent to introduction of the reservoir solution into the reservoir. In the former case, one may have to wait for equilibration of the test sample compound through the unit. In the latter case, one can inhibit the movement of the sample solution until diluted with the reservoir solution and then distribute the sample containing solution throughout the unit. Pneumatics, removable barriers, valves, etc may govern movement of the sample and the sample solution. This operation may be achieved by using a central dilution vessel into which the sample and diluent are added. The dilution vessel may have an interface with liquid in a channel for replenishment of liquid, which has evaporated.

Capillary channels would lead from the dilution vessel to one or more, usually a plurality of zones, where the diluted sample would migrate by capillary action to the individual zones. As appropriate, pneumatics, including a hydrostatic head, may be used to direct the flow of the liquids. The liquid from the dilution vessel would mix with other liquid(s) in the zone. In this way, small volumes of a reagent or candidate compound would be distributed among a number of zones for a subsequent operation, without initially having to manipulate small volumes. The same mechanism may be used to distribute an expensive reagent to a plurality of zones. In this situation, it may not be necessary to dilute the reagent, but the reagent may be directly added to the central vessel. The reagent would then be distributed from the vessel to the various zones. Desirably, the capillary channels will be relatively short, usually less than 1 cm, more usually less than about 0.5 cm and more than about 0.1 nm. The volume of the vessel will usually be at least 100 nl, more usually at least about 300 nl and less than about 1 ml, usually less than about 0.5 ml, depending on the amount of the solution to be transferred to each of the zones and the number of zones. By having a central vessel for distribution to a plurality of zones, one can reduce errors in transferring small volumes and provide for substantially equivalent transfer to a plurality of zones, allowing for direct comparison of results in each of the zones.

One may also have one or a multiplicity of vertical capillary channels comprising a terminal region having a larger cross-sectional area than the capillary channel and comprising a non-wettable region at or above the interface between the terminal region and the channel. The capillary would be placed in a reservoir to replenish liquid lost from the zone formed in the terminal region. As one added new liquid to the terminal region, initially the meniscus would be raised. Both evaporation and movement of the meniscus downward would occur, so that displacement of solution containing an active component would be minimized, keeping the volume of the zone minimal. The terminal region could be cylindrical, conical, or the like. Generally, the capillary channel would be circular, so that the terminal region would have at least about 1.2 times the capillary channel at the diameter at the non-wettable region, frequently at least about 1.5 times the diameter of the capillary channel at the non-wettable region.

In a first application, components are mixed and reduction of the volume of the mixture due to evaporation substantially precluded at the time of the addition by providing for contact with a solution in a channel, where the interface between the solution in the zone and the solution in the channel is relatively small, usually having a cross-sectional area of less than about 5 $mm^2$, usually less than about 2 $mm^2$, while being at least about 50 $\mu m^2$.

The solution added to the zone will normally involve a volatile solvent and may also include a non-volatile solvent, particularly where one or more of the components are not readily redistributed into the volatile solvent, e.g. water. Various non-volatile solvents include dimethyl sulfoxide, dimethyl fomamide, hexamethylphosphoramide, liquid organic salts, such as higher alkyl (>6) ammonium salts, polyethers, particularly polyalkylene glycols (alkylene of from 2–3 carbon atoms), such as dimethyl cellusolve, etc., where the volatility is in relation to the vapor pressure of water, where the vapor pressure of the non-aqueous solvent is generally at least half of that of water at ambient conditions. The solution may be introduced into the zone as described previously, where the method desirably assures a consistent amount of the solution being transferred. Alternatively, as described above, the solution may be distributed from a central vessel through capillary channels to a plurality of zones.

The zone is small and is the reaction mixture volume. Depending on the protocol, the zone may be contained in a region, e.g. space or gap, between two capillaries, on a platform, in a cylinder, a portion of a capillary channel, a chamber, etc. The zone may be contained in a vessel, e.g., a port or passageway, of sufficient depth to serve as a receiving vessel and/or a portion of the channel, underneath and/or adjacent to the port. The significance of the zone is that it provides the area of liquid exchange between the components of the added solution and the channel solution during the reaction. The zone has an opening that allows for access for addition of solutions, provides for liquid exchange between liquid in the zone and liquid in the channel, and permits evaporation. The channel will have a source of liquid for filling the channel, usually a reservoir, and normally be filled with the liquid prior to addition to the zone, which liquid will usually be buffer, including electrokinesis buffer, containing a component of interest, and/or reagent(s) or additive(s), or the like, necessary for the reaction to occur. The liquid will usually be an aqueous liquid, having at least 20 vol. % of water, usually at least 50 vol. % of water and may be solely water as the solvent. While one could add all of the components to the zone, so that need not be components, e.g. reagents or compound of interest, present in the liquid in the channel, it will usually be more efficient to provide at least one component in the channel solution, particularly where such component is relatively inexpensive.

In an embodiment where the channel serves as the floor of the zone or there is a floor to the zone, where a capillary channel outlet is in close proximity to the floor, a spatially restricted region will frequently be present extending upwardly beyond the periphery of the channel outlet. The region may have walls that extend beyond the top of the wall of the capillary channel. The zone may be all or partially contained in a receptacle that has a lower surface, usually a floor, and an adjacent portion of the wall that can be wetted, and at least a portion of the walls, mainly a portion distal to the channel interface will be non-wettable, so that aqueous media will be primarily restricted to the lower portion of the receptacle.

Depending on the nature of the walls of the receptacle or partial enclosure, the walls may have to be modified to provide the different properties. Non-wettable walls may be made wettable by coating with an appropriate hydrophilic composition, e.g. polymers, such as polyacrylates, having hydroxy- or aminoalkyl substituents, hydrolysis of hydrophobic polymers having functionalities which can be hydrolyzed to polar functionalities upon hydrolysis, proteins, polysaccharides, polyalkyleneoxides, etc., oxidizing the surface with ozone or other oxidizing agent, functionalizing the surface by the introduction of hydroxyl, carboxyl or amino groups, etc. For creating a non-wettable surface from a wettable surface, one may coat with a higher hydrocarbon or hydrocarbon derivative, such as grease, wax, lipid, oil, etc., a hydrophobic polymer, such as polyethylene, polyamide, etc.

In operation, a component of interest is provided in the zone, usually being added as a solution, where during the operation, none, all or part of the solvent may have evaporated. Alternatively, one may add a powder, gel or other form of the component of interest. The component may be obtained in a variety of ways being accessed from a robotic source of a large number of different components, a dispenser of a common component, or the like. In some instances, two or more components may be combined and incubated prior to addition of the mixture to the zone. In some instances, solutions may be obtained from microtiter plate wells, where the inlets and zones are positioned for receiving the contents of the wells into the zones. Microtiter plate wells usually have 96×n wells, where n=1–4. In this situation, one may use pins, with surface contact transfer, electrical fields, inertial forces, piezoelectric, electroosmotic force or a pressure differential to transfer the liquid in the wells to the subject zones. Generally, the volumes being transferred from the microtiter wells will be very small, being in the range described previously.

In view of the small volumes being transferred, evaporation will frequently be rapid, and may leave a dry residue of the components of the solution in the zone. The volume selected for delivery may be small enough, and the zone size and zone bottom large enough, that the solution will adhere to the bottom of zone without significantly entering or even contacting the channel inlet, where evaporation of the added solution is acceptable. Preferably, the parameters will be selected so as to inhibit evaporation to dryness.

In one embodiment, the microfluidic device will comprise a layer or substrate of plastic, glass, silicon, or other convenient materials, which may be hydrophilic, hydrophobic or combination thereof. The device will usually have a network of various channels and receptacles formed in the substrate and conveniently enclosed with a cover of the same or different material. Orifices can be provided in the cover or substrate, which orifices may serve as receptacles. There are many different methods of fabrication of the microfluidic network, which have been described in the literature. One may have a common source of liquid, which includes a manifold having a plurality of branches which provides liquid to a plurality of common channels, much in the way risers are used in plumbing in apartment buildings.

A zone which may be included in a partial enclosure and optionally a capillary channel in conjunction with other microstructures may be considered a unit. Where the subject device is to be used with microtiter well plates, each unit associated with a microtiter well would have a zone comprising at least one channel inlet, usually two opposed channel inlets. Depending on the protocol and the means of transport of fluids, one may use electroosmotic force, where there would be an independent pair of electrodes for moving liquid, or have a common electrode associated with a plurality of electrodes to provide the opposite polarity to the common electrode, with the electrodes in contact with the units. In an embodiment with individual pairs of electrodes at each unit, the operations usually would be confined to individual units having a single zone, rather than moving the composition to different sites and carrying out additional operations, although the individual pairs of electrodes could be used to provide a moving wave electrical field as described in U.S. Pat. No. 5,750,015. Thus, the substrate would provide for electrokinetic channels and the ability to receive electrodes or have the electrodes painted, adhered or otherwise present on the substrate.

However, one could provide for layered channels, where one would have additional channels connected to the unit channels that are normal to the plane of the unit channels. One would then have an additional microfluidic network for addressing the units individually and performing additional operations on the compositions. When used with microtiter well plates, once can provide for a microfluidic network having the zones positioned to be in alignment with the wells of the microtiter well plates.

The component of interest may be all or partially dissolved and will reside in the zone. The liquid in the capillary channel may be present in the zone or may be discharged into the zone, where the liquid will retain continuity between the liquid in the zone and the liquid in the capillary channel. Various means can be employed for pumping the liquid from the channel into the zone, including electrokinetic, pneumatic, mechanical, sonic, capillary, thermal, or the like. While the particular mode for moving the liquid into the zone is not critical, many advantages accrue by using electroosmotic pumping, where small volumes can be moved in different directions by changes in direction of an electrical field. Where electroosmotic pumping is used, one requires a channel with a region where the walls are charged or the solution includes a soluble charged polymer, such as an aminodextran, so that ions in the liquid of opposite charge to the wall charge accumulate at the wall. In the presence of an electrical field, the ions adjacent to the wall will move toward the electrode of opposite charge and carry liquid with them, providing a liquid pump. In this way, one can push liquid with significant precision from the channel into the zone and then withdraw the liquid in the zone back into the channel. The pump can be used to move liquid, which is not under the influence of an electrical field, diminishing electrokinetic separation in the solution. By this means, one may move liquid in defined volumes containing components, which may be adversely affected, by an electrical field. Alternatively, one may use pneumatic devices to move the liquid.

In order to automatically determine when the desired liquid volume has been introduced into the zone, rather than relying on the parameters which were used to pump the liquid into the zone, such as voltage, time, temperature, etc., one can provide for a detection system. One system uses an ionic medium, conveniently introduced into a channel connected to the zone, with a detection electrode in the ionic medium connected to a voltage source or ground. When electrokinetic pumping is employed, there will be an electrical field in the fluid. When the fluid in the zone contacts the ionic medium, a circuit will be formed with the detection electrode, which can be detected and further pumping terminated or the electrical field will be grounded and further pumping stopped. One may simply have an electrode in the zone, which when contacted with the liquid from the channel will act as described above. Instead of an electrical detection system, one may use an optical system, which detects the extent to which the liquid has penetrated the zone. The particular mode of detection will depend to some degree on the choice of the mode of transferring the fluid into and out of the zone.

If desired, evaporation during the course of the reaction may be impeded by closing the zone to the atmosphere, where feasible, adding a solvated polymer to the solution, and the like. A polymer may have the further advantage of reducing diffusion of the components from the zone into the channel solution. Polymers, which may be used, include polyethylene oxides, polypropylene oxides, ethers and esters of such polymers, polyacrylamides, dextran, modified dextrans, or other polymers which are water soluble. Generally, such polymers would be present in less than about 5 wt. % of the solution, preferably less than about 1 wt. % of the solution.

In the situation where the solvent substantially evaporates prior to dissolution in the channel liquid, the volume of liquid discharged from the channel may serve to concentrate the components from the well.

Where the zone is formed by expression of fluid from a channel, the fluid in the zone, during the brief period after introduction of the fluid from the channel into the zone, is prevented from significant reduction in volume by the reservoir of fluid in the channel. The fluid in the zone can be rapidly drawn back into the enclosed channel with substantially the same volume that was introduced from the channel into the zone and whatever fluid was present from addition of fluid to the zone, which has not previously evaporated. The zone solution may be withdrawn into the channel as a defined volume. One now has a defined volume of fluid as the zone in the channel, which will substantially retain its composition, since diffusion can be relatively slow. Furthermore, since some evaporation will occur at the channel outlet, the liquid will flow in the channel toward the zone, reducing movement of components away from the zone. In addition, by using microfluidics and electrokinesis, the zone may be moved to any site in the microfluidic network and be subject to various operations, such as the addition of reagents, separation of components, heating, cooling, etc., without significant change in its composition.

In another mode, one may employ opposed capillary channels to provide a continuous liquid fluid column as part of the manipulations of the various components. In this embodiment, the stream extends from one channel to the opposed channel through the zone liquid during the operation of the unit. At one or more different times, there may be a break in the column, particularly, where the column may be interrupted in the zone area. One may initially have liquid in one or both capillary channels and/or in the zone area. There may be a plurality of zones, which are not separated by walls from each other, being gaps between a plurality of channel outlets. In this situation, the opposed capillary channel outlets would be relatively close to each other, generally spaced apart by not more than about 5 mm, usually not more than about 2 mm, and preferably not more than about 1 mm. In this manner, one may have a plurality of opposed capillary channels in a block, which are separated by a gap, where liquid may be discharged from one or both capillary channels to cross the gap and form a continuous liquid column.

The openings of the channels at the gap are conveniently in the range of about $10^2$ to $5\times 10^5$ $\mu^2$. The volume of liquid in the gap will usually be in the range of about 1 to about $10^3$ nl. The liquid droplet between the opposed channels serves as the zone for addition of solutions. Various methods may be used for addition to the liquid in the gap, as described previously. Generally, each individual addition to the gap liquid or zone will not exceed about 500 nl, more usually not exceed about 250 nl. As appropriate, after each addition to the gap liquid or zone, the solution in the gap may be withdrawn into a channel and incubated and the signal then determined or discharged from the channel and the signal determined without interference from the device composition. The opposed channels may be provided in blocks comprising a plurality of channels, where one could have a planar array of opposed channels, as described in FIGS. 3 and 5, where the chamber is substituted with a gap. Addition could then be made at each gap from an array of devices for transferring liquids in small volumes and the manifold could be as depicted, or one could have different main channels providing different solutions for the different rows of units. In this way, devices can be provided which have 20 or more units, up to 2,000 or more units.

The size of the zone will be affected by the sizes of the ports, outlets and channels, volumes of the solutions added to the zones, the amount of liquid in the channel into which the components of the added solutions diffuse, by the nature (regions of wettability and non-wettability) of the walls enclosing the zone, the rate of evaporation, which may be related to the humidity, depth of the zone and air flow above the zone, the time of the reaction, the temperature, the composition of the solution in the channel, particularly as to the solution viscosity, and the like. Generally, these parameters will be selected to provide a dilution in the zone of the sample component added to the zone in the range of about 0.1 to 10:1, during the course of the reaction. Incubations may involve from about 1 min. to 24 h, usually not exceeding about 12 h. The reaction time will usually require at least 1 min., usually at lest about 5 mins, and not more than about 6 h, usually not more than abut 2 h. Ambient conditions will usually suffice, with temperatures below about 60° C., more usually not more than about 40° C. In some situations where thermal cycling is involved, temperatures may be as high as 95° C., usually not exceeding about 85° C., and cycling between 45° C. and 95° C. Heating can be achieved with lasers, light flashes, resistance heaters, infrared, heat transfer, conduction, magnetic heaters, and the like.

Components of interest for use in many of the determinations include small organic molecules about 100 Dal to 5 kDal in molecular weight, more usually not more than about 2.5 kDal, oligopeptides, oligonucleotides, and oligosaccharides, proteins, sugars, nucleic acids, microsomes, membranes, cells, organelles, tissue, etc., where the components may serve as ligands, receptors, enzymes, substrates, cofactors, functional nucleic acid sequences, e.g., promoters and enhancers, transcription factors, etc. Reactions of interest will include binding reactions, which may involve enzymes, receptors, transcription factors, nucleic acids, lectins, and the like, where inhibition, activation, signal transduction, antagonists, and chemical reactions may be involved. Various protocols and different device structures may exemplify the subject devices.

In one exemplification of the use of the subject devices employing microtiter well plates, the microtiter well plate will have solutions which are to be analyzed, but lack one or more components necessary for the analysis. These solutions will usually be constituted to determine a binding event, interactions between two moieties, the presence of a particular moiety, and the like. The solutions in the wells may involve a single compound to be tested, a mixture of compounds including a test or control compound, or the like. Normally, there will be different compositions in different wells. The wells may involve heterogeneous binding, where a component of the determination method is bound to the surface of the wells and will be retained in the well. For example, in a specific binding assay, one may have receptors bound to the surface of the well and allow for a competition between a test compound and a labeled analog for binding to the receptor. After incubating the mixture in the well, the mixture is transferred to the microfluidic device zone and the label determined. Where the label is an enzyme, the liquid in the zone could include substrate for the enzyme, where the product of the substrate would provide a detectable signal. Alternatively, the label could be a fluorescer, where one would read the fluorescence in the zone. In both instances, the determination could be made in the absence of bound label.

There is also the opportunity to perform a heterogeneous assay in the zone. By having a bound entity, e.g., compound, cell, tissue, etc., for which the candidate and control compounds compete, where the bound entity is in limited amount, one can determine the activity of the candidate compound. By limited is intended that it is insufficient to bind more than about 75%, usually about 50%, of the total number of molecules of candidate and control. In carrying out the determination, the candidate or test compound and control are added to the zone. The bound compound is in the zone, bound to any surface associated with the zone, including walls, which includes the walls of the zone enclosure and channel walls, particles and the like.

For example, one may coat the region surrounding the zone with an entity, e.g., cell, compound, etc., where the entity becomes bound in that region. The channel is then filled with a solution and the candidate compound and control compound added into the zone. The candidate and control compounds will compete for available binding sites of the bound entity. After sufficient time for reaction to occur, one may move the liquid in the zone. The system allows for the addition of very small volumes to a reaction mixture, where the dilution of the volume(s) may be controlled by the size of the zone. During the competitive binding reaction, the competitive compounds will be substantially retained in the region. Removal of the control compound and washing of the region is readily achieved by moving the liquid column in the channel, and one can readily detect the signal in the channel.

To enhance the surface area associated with the zone, one may have a wettable porous membrane between the channel and zone interface. The membrane may serve a number of functions, retaining particles in the zone, providing surface for binding entities, acting as a filter, and the like. Particles may be introduced into the zone and held in position by a variety of ways, through covalent or non-covalent bonding to the walls, barriers to movements, such as protrusions, cross-bars, magnetic particles, etc.

Instead of a heterogeneous system, namely a system requiring binding to a surface and a separation, one may use homogeneous assay protocols. Homogeneous assays may be exemplified by EMIT, FRET, LOCI, SLFIA, channeling assays, fluorescence protection assays, fluorescence polarization, reporter gene assays using whole cells, particle labels, etc., where enzyme, particle, fluorescer and chemiluminescer labels are employed. In these assays, one does not require a separation, since the binding event changes the level of observed signal. One would carry out the protocol in the same manner, but for the binding of the bound compound and the separation step, as the assay requiring the separation, where the liquid in the channel could provide one or more reagents required for the determination of the signal and/or provide a convenient site for detection of a signal.

In some instances one may wish to monitor the effect of a test compound on enzyme activity. In this situation one may add the test compound and enzyme to the zone comprising the channel solution, which provides the substrate. After sufficient time for reaction to occur, one may then determine the extent of the enzyme activity in the presence of the test compound.

Other assays of interest involve the effect of a test compound on the association of two other compounds, usually proteins, as members of a complex. These associations include transcription factors, cell surface receptors with other proteins, e.g. G-proteins, proteins binding to nucleic acids, e.g., DNA, lectins with sugars, subunit associations, etc. These assays may be carried out in substantially the same way as the heterogeneous assay, where one member of the complex is bound to the zone surface. However, in this case, instead of using a labeled member of the complex, the liquid in the channel could provide for an assay of the complex m. ember. First, one would combine the candidate compound and the two members of the complex, either in a well or in a zone. The amount of complex formation and, therefore, amount of free uncomplexed members would be related to the effect of the candidate compound on complex formation., Once there has been sufficient time for complex formation, the determinations in each zone could be performed. By performing assays where a common liquid is used for all of the zones, one can perform a number of discrete steps. For example, since the complex member to be measured would be common to all of the assay determinations, one could provide for capture of the complex member in the channel portion of the zone, e.g. by having specific antibodies for the complex member. One could then wash out all of the channels using buffer, and then add a second solution comprising labeled specific antibody, which would bind to any of the complex member captured in the channel. With a fluorescent label, one could detect fluorescence. If one does not wish to capture the complex member, one may use several of the homogeneous assays and determine the level of the complex present in the zone.

One may use cells or compounds that are bound to the surface in the zone. These cells or compounds may serve a variety of functions, such as local buffering, production of agents to interact with agents in the zone, interacting with agents from the zone, production of detectable signals, etc. For example, by using polymers comprising buffering agents, the acidity or alkalinity of the solution in the zone may be controlled. Where a product is produced in the zone, which can bind to a surface membrane receptor of the cell and transduce a signal resulting in expression of a detectable product, the production of such product, may be monitored by the signal produced by the cell. Various compounds are known to bind to surface membrane receptors and transduce signals, such as steroids, hormones, interleukins, growth factors, etc., and biomimetric analogs thereof. By having a reaction in the zone that results in an active ligand, diffusion of the ligand to the cell, will result in the transduction of a signal. By having a regulatory region, e.g. promoter and/or enhancer, responsive to the transduced signal, where expression results in a detectable product, e.g. green fluorescent protein, an enzyme that catalyzes a detectable product, etc., one can monitor the rate at which the ligand is produced. Where one is screening for compounds, which activate or inhibit formation of the ligand, the production of the detectable signal would indicate the activity of a candidate compound.

With appropriate controls, one may take aliquots from the microtiter plate wells or other source of reaction components, so that one may obtain a plurality of determinations from a single mixture. In some situations, it may be feasible to control the volume transferred to the zone by using the detection systems described for determining the volume of liquid discharged from the channel. Alternatively, one may have detection systems in the zones. Other monitoring methods may also find use. One would then carry out an individual operation with a first microfluidic device, remove the device and replace it with a second fresh microfluidic device, and so on. When dealing with rare agents, such as test compounds, there would be minimal loss of the test compound during the operations and one could obtain a plurality of determinations about the test compound. One could directly move a test compound in a microtiter plate well from the well through an opening in the zone into the capillary channel containing a reaction medium. After sufficient time for reaction to occur, one may then read a signal through the opening.

Of interest when measuring a signal is the presence of an orifice in the channel above the liquid, which allows for evaporation at the site of the determination, where the area in and optionally below the orifice serves as the zone. The solution of interest in the zone is bordered by liquid, so that the adjacent fluid acts as a reservoir for replenishing the liquid, which is lost by evaporation. This results in fluid flow toward the zone, which maintains the solutes in the zone, so that there is less diffusion away from the zone of the signal producing components during the time of measurement. By having a region associated with the zone of diminished area at which there is liquid exchange, diffusion is diminished, while liquid replenishment occurs. For example, in the case of a passageway through the wall of a capillary channel, which serves as at least a portion of the zone, the cross-section of the capillary channel is chosen to discourage significant diffusion from the region underneath the passageway. The reduction in the rate of diffusion of components from the zone allows for accurate rate determinations, since the change in signal will be substantially larger than the reduction in signal resulting from diffusion away of the signal-producing moiety.

The subject devices allow for a wide variety of applications. In one application, one may introduce a drop of a solution containing one or more components or reagents from a channel into the zone, either prior, subsequent or concomitant with introducing a test component through the orifice, where one is interested in the binding of the test component to a reagent in the liquid mixture. One would then withdraw the liquid in the zone into the channel, preventing any significant evaporation. The mixture could be incubated for a predetermined period of time. By providing that binding of the test component to the reagent results in a detectable signal, one can determine the binding of the test component to its target. For example, a reagent which is a complex of a protein target and a known ligand, where the protein is conjugated with quencher and the ligand with a fluorescer, release of the ligand will result in a fluorescent signal. By measuring the increase in fluorescence as a result of the test component binding to target protein and displacing the fluorescent ligand conjugate, one can determine the binding affinity of the test component to the target protein.

An alternative assay could use the opposed channels separated by a gap having a floor. In the gap one would bind different enzyme alleles at different spaces on the floor between each of the pairs of opposed channels. A solution of a compound would then be passed through the opening created by the gap and the mixture allowed to incubate, while in contact with the liquid in the channel. After sufficient time, a solution of the substrate would then be directed from the other channel into the gap to join with the liquid from the opposing channel. In this way substrate would be continuously supplied from the other channel. The turnover rate of the enzyme would be determined by detecting product in the gap, where the turnover rate would be constant, or increase with time. The rate would be related to the inhibitory effect of the compound and its binding affinity. For different alleles, one could have a single source or manifold of substrate solutions for supplying the individual channels where electroosmotic force could be used for pumping the substrate solution through the channels. This device allows one to rapidly determine the effect of a compound on different alleles. Rather than different alleles, one could have different enzymes and have different substrates in the different channels and any combination of related or unrelated entities.

In another method, one would have a continuous liquid column with opposed channels and gaps between the channels to define zones. Mixtures of enzymes and candidate and control compounds would be prepared and added to the zones, simultaneously or consecutively. After sufficient time of incubation, the liquids in the wells would be introduced to the zone. In the channels would be an appropriate substrate buffer solution. The solutions would mix with the buffer solution and evaporation would occur. The effect of the evaporation is to maintain the product narrowly confined to the zone as a result of liquid flow from the channels into the zone to replace the liquid lost by evaporations. By providing for production of a detectable product, one could determine the effect of the compounds on the enzymes.

In a further method, one would transfer a solution into an orifice or passageway in an otherwise enclosed channel into the zone and allow the solvent to evaporate. The solution would form a droplet on the surface of the channel and leave its components on the surface as a small spot. The components could be cells and a candidate compound for a cell surface receptor. The cells would adhere to the surface. Liquid would then be expressed from the channel into the zone, or a reservoir(s) filled to direct liquid into the zone, where the channel liquid introduced into the zone would have a ligand conjugate, for example, a fluorescent conjugate. After allowing sufficient time for the fluorescent conjugate to bind to any available receptor binding sites, the liquid would be withdrawn into the channel away from the zone and the fluorescence read. If liquid were necessary for the reading, a different liquid could be introduced into the zone through the orifice or from the reservoir. The binding of the candidate compound would be determined by the reduction in fluorescence in the zone.

Obviously, there are too many operations which may be carried out, employing different diagnostic assay reagents, different targets and different protocols, to exemplify all of them, so that only a few have been illustrated as exemplary of the subject methodology.

The device may provide for heating and cooling of the zone. By varying the temperature of the channel, a large heat sink or source is provided for the zone. By having means for heating or cooling the fluid in the channel, one can modify the temperature of the zone, cycling the zone temperature in relation to the channel. To provide for more rapid variation in temperature, one may provide for heating and/or cooling solely in the zone, where once the source of thermal variation in the zone is terminated, the zone would rapidly equilibrate with the temperature of the channel. For example, in thermal cycling, one could use microwave heating, RF heating, laser heating, or the like, where the electromagnetic heating source is focused on the zone, so as primarily to change the temperature of the zone. In processes involving thermal cycling, such as the polymerase chain reaction, one would rapidly raise the temperature of the zone to 85–95° C., while maintaining the channel temperature at about 35–50° C. Once the DNA has been denatured, which would be a matter of not more than about 2 or 3 minutes, usually less, by removing the source of heat, the liquid in the zone would rapidly equilibrate with the temperature of the liquid in the channel. By appropriate selection of the temperature of the liquid in the channel, the temperature profile during the cycling may be controlled to provide the desired times for the different temperature stages of the cycle.

The amplification may occur in solution or on beads, as in bridged amplification. See, for example, U.S. Pat. No. 5,641,658. By having the source of the DNA in the channels, all of the zones may include the same DNA or by providing different DNA in different channels, different zones may have different DNA. Conveniently, the channels may also provide the dNTPs and primers, or the dNTPs and primers may be added to the zones. By adding the DNA polymerase to the zone through the orifice to the zone, the reaction may be initiated and cycled to amplify the DNA. After completion of the thermal cycling, the amplified DNA may be used for sequence determination, identification of particular sequences, using probes, snps may be identified or other characteristic of the amplified DNA may be identified. Various protocols exist for identification of complex formation between a probe and target DNA, which may occur in the zone or as a result of analysis outside of the zone.

The subject systems may be used with many other ancillary systems to further enhance the flexibility and variety of operations for the system. One combination is with electrokinesis, where the zone would be part of a channel in which an electrical field is employed. By having reservoirs at opposite ends of the channel or using the zone as one reservoir, by applying an electrical field across, the zone, charged species could be moved from the zone into the channel. Alternatively, one may use electroosmotic pumping to move the liquid in the zone to another site. By having crossed channels in the electrokinetic unit, components of the zone may be moved to an intersection and a defined volume injected into the second channel, where the defined volume may be subjected to different operations. The defined volume may be analyzed by electrophoretic separation, where the result of the operation in the zone is to have two or more detectable species having different mobilities in electrophoresis. One can provide for a detector along the second channel to identify the detectable species and quantitate the detectable species. Since one would be able to quantitate the initial and final agents, one would have a material balance.

The zone may be combined with other devices for separation, analysis, etc. These devices may be HPLC columns, which may be miniaturized, connectors to gas chromatographic devices, mass spectrometric devices, spectrophotometers, fluorimeters, etc. By providing for pneumatic movement of the liquid in the zone to a channel, which directs the liquid to the other device, the liquid in the channel may be moved from the zone to the site where it may be analyzed. One can withdraw samples from individual zones, by employing reduced pressure above the zone, which will withdraw liquid from the zone into the device for analysis. One need only have a small pressure differential between the channel and above the liquid in the zone to have the liquid in the channel chase the liquid in the zone to a different site.

For the devices, large networks of channels may be produced in small integrated devices using a solid substrate, plate, block or film, commonly referred to as a card or chip, having one dimension ranging from about 5 mm to 10 cm and a second dimension ranging from about 5 mm to 50 cm, usually not more than about 20 cm, and preferably not more than about 10 cm, where the thickness may or may not be critical. In many cases, microstructures, such as channels and reservoirs may be formed in one substrate and the microstructures, enclosed as appropriate, with a cover or other substrate. The thickness of the device will depend on a number of factors, generally ranging from about 0.2 mm to about 5 mm, more usually from about 0.5 mm to about 2 mm. The thickness of the layers will determine, in part, the height of the ports and the dimensions of the channels, particularly channel height. Depending on the structures and protocols, there may be no orifice, the zone open to its environment being present in a gap or being in a part, channel or combination thereof. The part in the cover or base layer may have a depth as small as 1 $\mu$m and will usually be less than about 3 mm, generally being in the range of about 100 $\mu$m to 2.5 mm. Where there is a combination of a port and channel, desirably the port will have a height of at least about 0.1 mm, and may be 2.5 mm or more, usually less than about 1 mm. One may have as many individual units as space allows, desirably having at least about 12, more usually at least about 36 and up to 2,000 or more.

When having ports in channels, where the port comprises at least a portion of the zone, the chip will usually be comprised of at least two layers, a base layer comprising depressions or cavities, which may serve as channels, chambers, electrode contacts or connectors, and optionally ports to the depressions and cavities, and a cover layer, which encloses the depressions and cavities and may alternatively provide ports to the depressions and cavities. Additional layers may be present, laminated to the substrate, such as heat transfer layers, supports, casings, where films are used as the substrate and cover, and the like.

In FIG. 1, a fragment of a device is shown in perspective. The device 10 comprises a first layer substrate 12 of sufficient thickness to accommodate the features for the operation of the device 10. Sealed to the substrate 12 is base 14. Embodied in the substrate are units 16. Each of the units comprises a reservoir 18 in which contact electrode 20 extends from surface wire 22. The contact electrodes 20 and surface wires 22 may be wires, electrically conducting paint, or other means of electrical conduction. The surface wires 22 are connected to a controlled voltage source for providing an electric potential in accordance with a predetermined regimen. The reservoir 18 has port 24, for allowing communication with the atmosphere, and may be employed for introduction and removal of materials into and from the reservoir 18. Chamber 26 has port 28, where chamber 26 differs from reservoir 18 in its function, and will usually have different dimensions from reservoir 18. For operation of the device, the evaporation per unit area in the chamber will be greater than the evaporation per unit area in the reservoir. For the most part, the cross-section of the chamber 26 will be smaller than the cross-section of the reservoir, generally being smaller by at least about 10%, usually at least about 25%, and not more than about 90%. Normally, there will not be an electrical connection in chamber 26, although an electrode may be employed for monitoring the presence and or amount of fluid in the chamber. Adding an additional wire to the device can be readily accomplished in the same manner as the electrical connections for the reservoirs 18. Not shown is an optical detector, which could be used for detection of the presence or amount of liquid in the reservoir 18. Reservoir 30 is substantially the same as reservoir 18 in having contact electrode 32 in electrical connection with surface wire 34. Reservoir 30 is optional, but may be present where greater versatility is desired in the device, rather than only a single chamber and a single reservoir per unit. Horizontal channel 36 provides fluid connection between the reservoirs 18 and 30 and the chamber 26. Finally electrode 38 extends through substrate 12 into horizontal channel 36 and is connected to surface wire 40 for connection to a control device.

Depending on the manner of the use of the device, the surfaces of the various parts may vary, as to wettability and charge. For example, the upper portion of the inner wall 42 of the chamber 26 may be coated with a hydrophobic material to prevent aqueous media from rising up the wall. The region 44 in the channel 36 under the chamber 26 will be desirably wettable, so that aqueous solutions introduced into the chamber will wet the surface. Depending on what form of electrokinesis is used, electrophoresis or electroosmotic force (EOF), the surfaces of the channels will differ. For electrophoresis, it is desirable that the surface be neutral, while for EOF the surface should be charged, although by using an electrically charged water soluble polymer in the aqueous medium, where the charges are randomly distributed, neutral surfaces can be used. Charged surfaces may be achieved by using silicates, e.g. glass, charged coatings, covalently bonded or adhering, to the surfaces, or modifying neutral surfaces chemically to introduce charged species. Neutral species may be a variety of polymers, both addition and condensation polymers, particularly acrylates, although polystyrenes, polyolefins, etc. find use. Different regions may have different charge and functional characteristics. For example, a portion of a structural feature may be charged to permit EOF and another portion be neutral, where the charged portion is a conduit for movement of fluid under the urging of the EOF flow. During operation, there will be a fluid in at least one of channels 18 and 30 and at least a portion of channel 36, and there may be fluid as well in chamber 26, where there would be a continuous or discontinuous stream in the unit.

Figures 1, 2A:
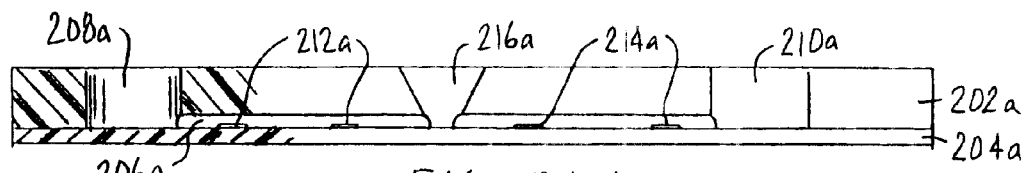
Figure 2A:
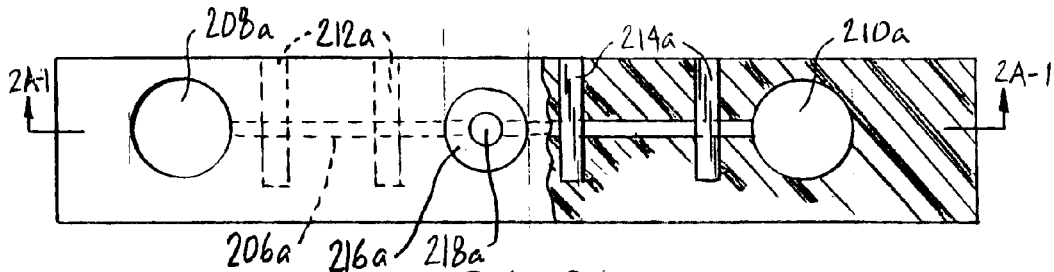
Figures 1, 2B:
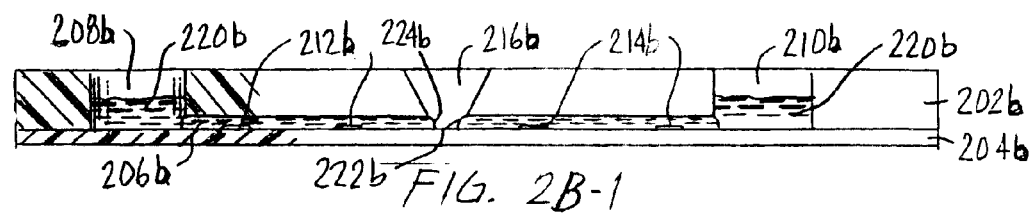
Figure 2B:
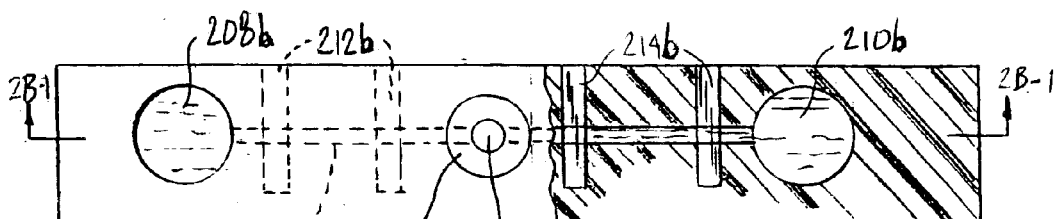
Figures 1, 2C:
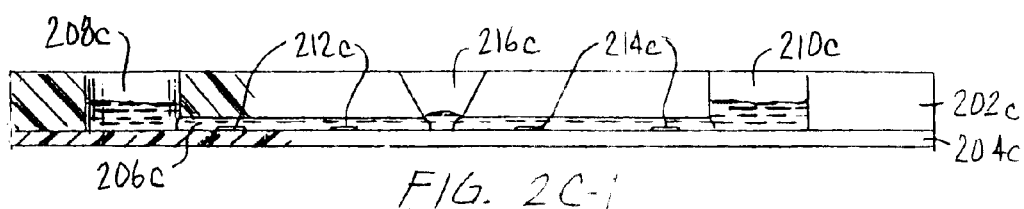
Figure 2C:
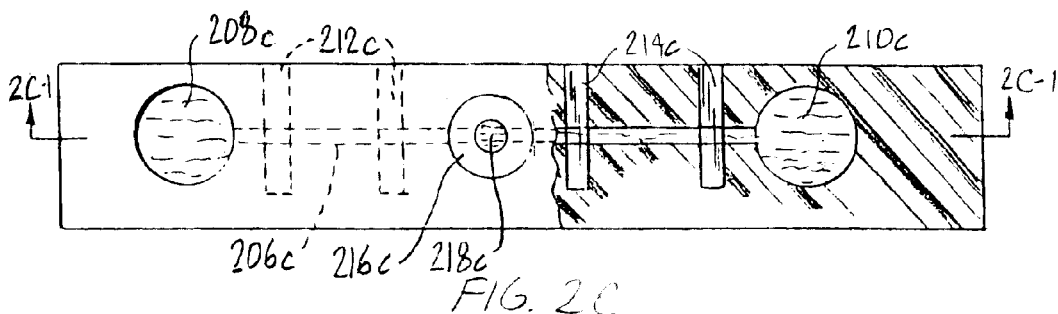

In FIGS. 2A, 2B and 2C, are depicted diagrammatic cross-sectional views of a unit in a device. The unit device 200a has substrate 202a, in which the various features of the unit device are present, and cover 204a. The unit comprises a channel 206a, which may be connected to a common manifold for receiving a medium common to all of the units. Each unit has two wells 208a and 210a, where either or both may serve as wells for introduction of fluids. Situated in the channel 206a are two sets of electrodes, 212a and 214a, where the electrodes may be painted onto over 204a and chamber 216a all communicate with channel 206a. The surface 218a under chamber 216a, which is the surface of the cover 204a, is hydrophilic for acceptance of hydrophilic liquids. The unit is shown prior to introduction of any liquid.

In FIG. 2B, liquid 220b is introduced into the wells 208b and 210b. In the present configuration, the liquid is indicated as being the same, but with different protocols the liquid could be different. The liquid 220b from the wells 208b and 210b moves by capillary action into channel 206b and halts at chamber 216b, due to the absence of capillarity at the chamber 206b. A sample may then be added to chamber 216b, which will wet the surface 218b. Where the sample is small enough, it will not contact the inlet ports 222b and 224b of channel 206b. Depending upon the nature of the solvent added to the chamber 216b and the time interval in which the solvent is allowed to stand, all or a portion of the solvent may evaporate, so that upon total evaporation, only a solvent free liquid or solid will be present.

In FIG. 2C, contact is made between the material in the chamber 216c and the liquid 220c. Liquid 220c may be expressed into chamber 216c using one or both pairs of electrodes 212c and 214c, using EOF for moving the liquid 220c. As shown in FIG. 2C, the channel 206c is filled with the liquid 220c, so as to form a continuous stream of liquid. However, it is not necessary to have a continuous stream, and if desired, the stream may be discontinuous, where fluid is driven by only one set of electrodes and is stopped before making contact with the fluid in the channel 206c on the other side of the chamber 216c. In the latter situation, one may wish to withdraw the liquid from the chamber into the enclosed portion of channel 206c to inhibit evaporation of the solution.

Figure 3:
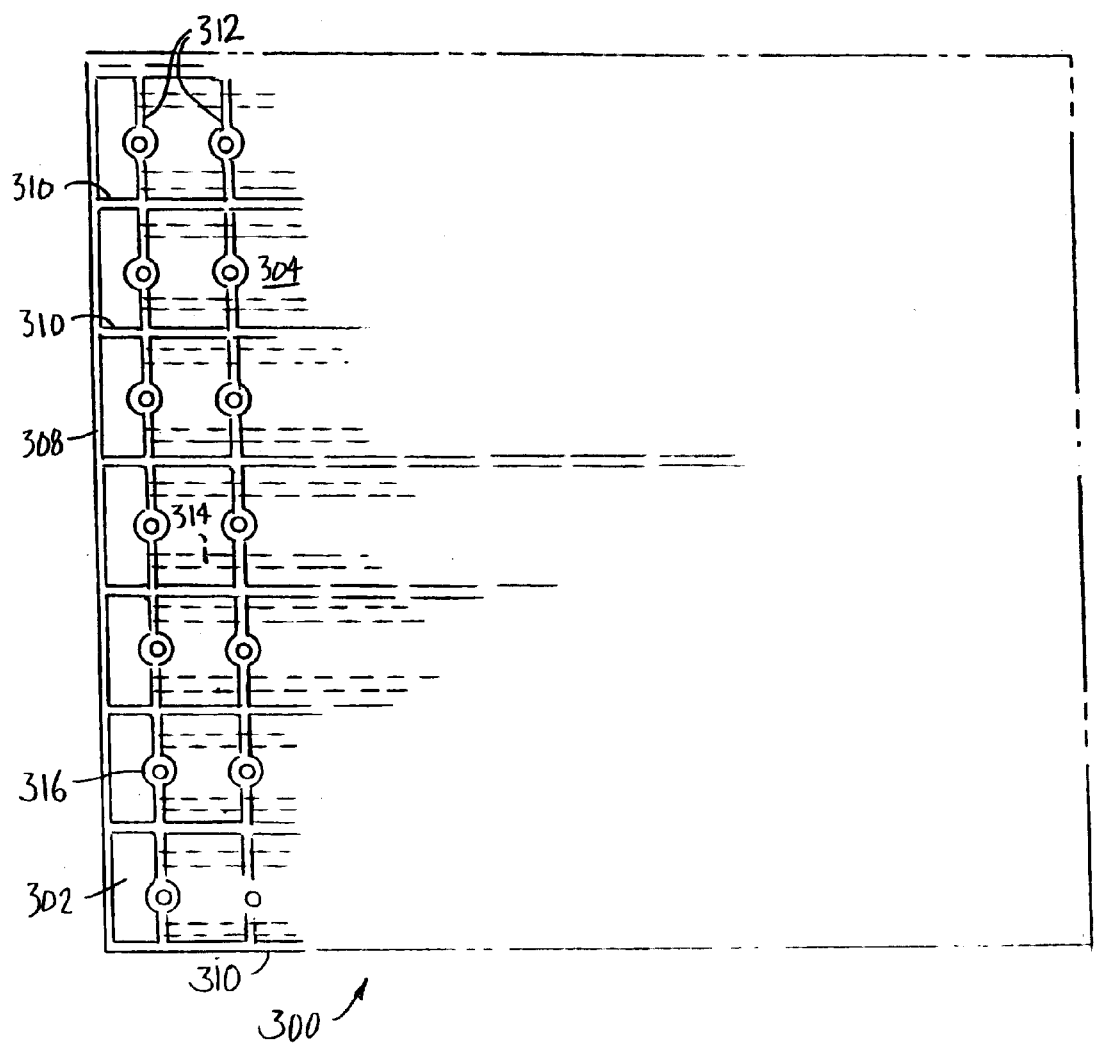
FIG. 3 is a diagrammatic plan view of a device with a plurality of units with fluid supplied by a manifold.

In FIG. 3, a diagrammatic plan view of a device is shown comprising a plurality of units and employing a common manifold for delivering liquid to the wells. This device is distinguished from the device depicted in FIG. 2 in having a common source of liquid, rather than allowing for different liquids to be available for different units. The device 300 comprises a substrate 302 and a cover 304, on which the substrate 302 is supported. The device has a common inlet port 306 and tributary channels 310. Each of the tributary channels 310 is connected to a plurality of side channels 312, which serve to provide liquid to chambers 316. Each side channel 312 is equipped with a pair of electrodes 314 for EOF pumping of liquid into and out of chambers 316. Liquid introduced into the inlet port 306 will move by capillary action through the channels 308, 310 and 312 to fill the manifold, but not enter the chambers 316. Different samples may be added by any convenient means to each of the chambers 316 and the sample may be further processed. Usually, with an aqueous sample there will be rapid evaporation. By using the pairs of electrodes 314 associated with one of the two side channels 312 associated with each of the chambers 316, a small volume of the liquid in the manifolds may be pumped into the chamber 316 to dilute the sample and then be rapidly withdrawn back into the side channel as a defined volume to allow for any incubation and inhibit further evaporation. The presence of the fluid in the channel in contact with the defined volume will replenish any of the solvent, which evaporates due to the presence of the inlet from the channel 312 into the chamber 316. In this way the composition of the defined volume will remain substantially constant in that the flow of solvent is into the defined volume and diffusion away of the larger components from the defined volume is discouraged. After sufficient time for any reaction to occur between the sample components and the components of the liquid, a reading may be taken of the defined volume in the channel or the defined volume may be pumped into the chamber 316 for taking the reading, to avoid having to read through the cover 304 composition. If one wishes to make a plurality of readings in the chamber 316, or even in the case where a single reading is made, the defined volume may be introduced into the chamber 316 and contact made with the liquid in the opposing side channel 312. Contact may be made by pumping the liquid from the opposing channel 312 into the chamber 316 or by adding enough volume from the channel containing the defined volume to bridge the floor of the chamber and join the fluid in the opposing channel 312.

The presence of the sample in the chamber in contact with the two side channels permits replenishment of liquid, which evaporates from the solution in the chamber. Diffusion of the components of interest is not significant, so that the loss of the components of interest in the zone is minimal and the signal from the solution in the chamber remains substantially constant over extended periods of time, particularly within the time frame of the usual measurements, generally under about 0.5 h. Since one is dealing with very small volumes, generally less than about 500 nl, substantial changes in composition could have an effect on the observed signal. For example, where one is interested in a binding affinity of a ligand to a receptor, a change in concentration of the ligand and/or receptor would affect the observed signal. Where one is interested in determining a rate, the problem is exacerbated, if during the assay, the concentration of all components of the solution are changing. Therefore, by permitting evaporation to occur in a zone of an assay mixture, while the zone is in contact with a solution which has substantially the same composition, except of one or few, usually not more than about 4, more usually not more than about 3, components, generally being the components of interest, many advantages ensue. Handling is easier, diffusion of the components having concentration gradients between the assay mixture and the liquid in the channel appears to be slower, and the solution can be read without the interference of the composition of the device. Generally, the liquid in the channel will be substantially the same liquid of the defined volume, except for the differing components of the sample introduced into the defined volume. Usually, the dilution factor of the sample in the zone will be in the range of about 0.1–10:1 during the course of the reaction.

Figure 4:
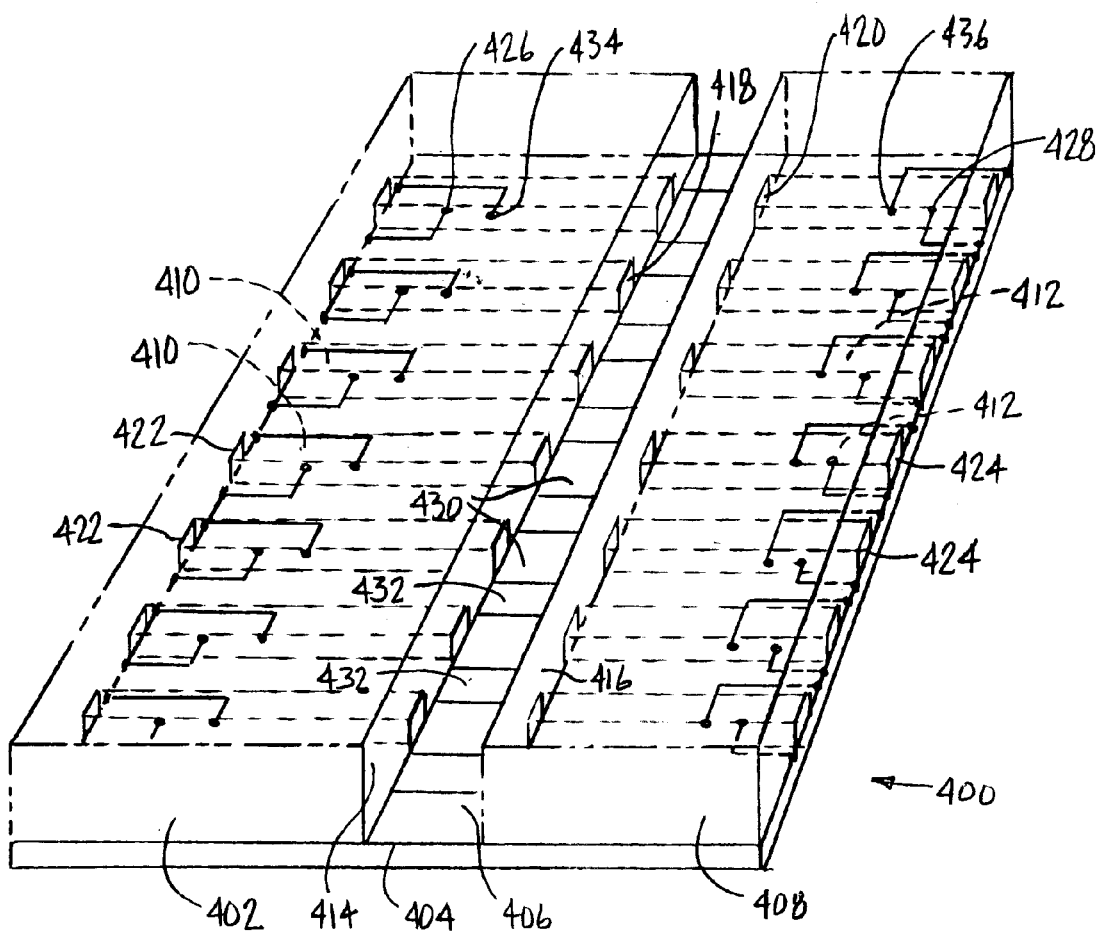
FIG. 4 is a fragmentary perspective view of an alternative embodiment of a microfluidic device with two channel blocks joined by a platform.

In a further embodiment, as depicted in FIG. 4, instead of having chambers isolated by walls, one has a platform between a plurality of capillary channels, where desirably each area between the channels on the platform is wettable and separated by a non-wettable zone. The device 400 has a first channel containing block 402, a platform 404, which may be open at its ends 406 and optionally, a second channel containing block 408, where the first and second channel blocks 402 and 408 are joined by the platform 404. The second channel containing block is not necessary since all of the operations may be performed with a single channel containing block, although there are advantages in having a source of liquid on both sides of a droplet on the platform. Each of the channel containing blocks 402 and 408 have a plurality of channels 410 and 412, respectively. Each channel 410 and 412 terminates at a block face 414 and 416, respectively, which is non-wettable, with outlets 418 and 420, respectively, allowing for liquid communication with the platform. Each of the channels 410 and 412 has an orifice 422 and 424. Fitted near the respective orifices in the channels are electrodes 426 and 428. Conveniently, the area 430 of the platform between the channel outlets 418 and 420 is wettable, separated from the next wettable zone by a non-wettable band 432. Into each channel is extended a second electrode 434 and 436, which can be used for controlling flow of liquid in the channels in conjunction with electrodes 426 and 428, respectively.

The spacing between the blocks 402 and 408 will vary, depending on the protocol, the size of the sample volume, the size of the defined volume to be used for the reaction, the surface tension of the liquid, the contact angle of the liquid, and the like. The higher the surface tension, the smaller the gap. Usually, the spacing will be at least about 0.05 mm and not more than about 2 mm, usually not more than about 1 mm. The spacing will affect the volume of the reaction mixture and the volume of sample, which may be set down without contacting the channel outlets. Generally, volumes of sample will be not more than about 300 nl, usually not more than about 100 nl, with the minimum amount being controlled by the ability to transfer the volume. The spaces on the platforms may be coordinated with a microtiter well plate, so that the sample may be received from individual microtiter well plates at each hydrophilic site. The sample may be pre-prepared, combining some but not all of the reagents required for a determination. The remaining reagents necessary for the determination would be contained in the liquid in a channel or could be divided between the two opposing channels.

In carrying out a determination, one exemplary protocol is as follows: A sample is pre-prepared comprising a compound of interest and some but not all of the reagents required for a determination. While one could have all of the reagents necessary for the determination in the sample mixture, using the subject device solely for maintenance of a liquid medium, generally one will prevent a premature reaction by withholding a necessary reagent from the sample mixture, which is provided by the liquid in one or both channels. The samples are placed on the wettable sites 430 and, as appropriate, evaporation occurs. The walls of the capillaries 410 and 412 are appropriately charged or the medium contains an appropriate additive to support EOF pumping. Liquid is added to the capillary channels 410 through orifices 422 in sufficient amount to allow pumping of the liquid to extend a droplet from channel outlet 418 of sufficient volume to capture and dissolve the sample mixture in the droplet to form a defined volume. This is achieved by providing the appropriate polarity between electrodes 426 and 434, depending on the charge of the wall of the channel 410. While not necessary, it may be desirable to withdraw the defined volume through outlet 418 into channel 410 to substantially inhibit evaporation. As discussed previously, little, if any, significant diffusion occurs, so that the defined volume retains substantially the same composition. Withdrawal of the defined volume into the channel 410 can be achieved by reversing the polarity of the electrodes 426 and 434 that was employed when expressing the droplet. The defined volume may be retained in the channel for a sufficient time for a reaction to occur. Where the reaction is completed in the channel, the defined volume may be interrogated in accordance with the signal generated by the reaction. Alternatively, to avoid interference from the block 402 composition, the defined volume may be expressed onto the surface 430 and interrogated directly. If desired, fluid may be introduced into channels 412, in sufficient amount to extend to the outlet 420. The fluid in channel 412 may be expressed and withdrawn much in the manner of the fluid in channel 410.

In some situations, one may wish to incubate the defined volume in the channel 410 and then express the defined volume onto the platform 404 at site 430. The defined volume may then be separated from the liquid in channel 410 by mechanical action, introduction of a physical barrier, or the like, and the solvent allowed to evaporate. The liquid in channel 412 containing an additional reagent necessary for the determination may then be expressed and contacted with the assay mixture at site 430, the assay mixture dissolved in the liquid to form a second defined volume, which may then be read or withdrawn into channel 412 for incubation. As described previously, the defined volume may be interrogated in the channel 412 or expressed onto the site 430 and interrogated at that site.

Quite clearly, depending upon the protocol, less or more sophisticated devices may be used. By having two channel blocks, which can be independently operated, highly complex and sophisticated protocols may be performed.

Figure 5A:
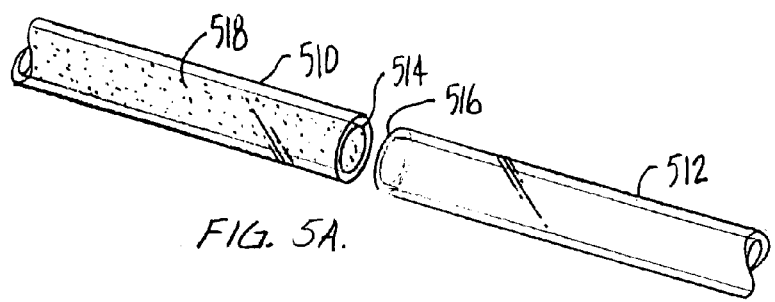
FIGS. 5A, 5B and 5C are perspective diagrammatic views of a device according to this invention employing two channels at different stages in their use.
Figure 5B:
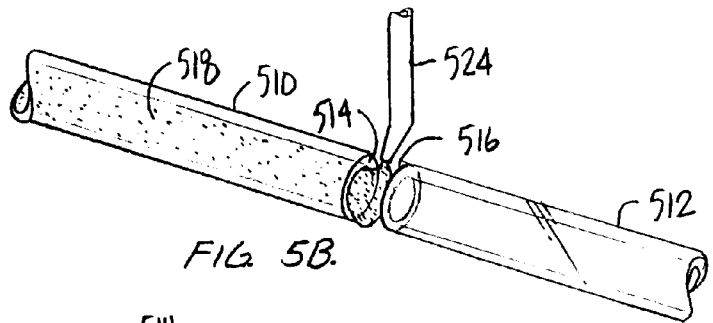
Figure 5C:
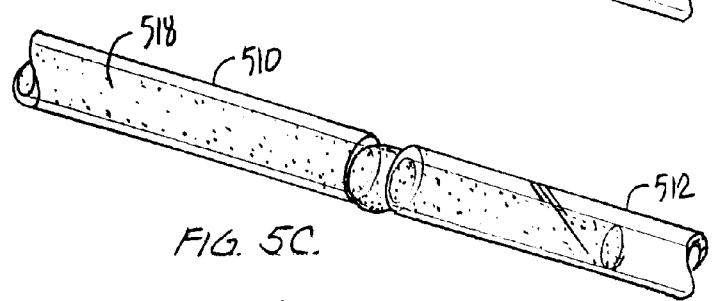

In FIG. 5, a simple structure is depicted of how two channels could be used in accordance with the subject invention. While only two channels are shown, it is understood that the two channels are only exemplary of a device having a plurality of channels, where blocks or plates are provided in which the channels are formed and main channels provided for carrying and removing liquid from the channels. Each channel in one block has a corresponding channel in the other block, which may be directly opposite or offset. The distance between the centers of the channel outlets will not exceed about 5 mm, where the distance between related channels will always be shorter than the distance to any other channel in the opposing block. As shown in FIG. 5A, a first channel 510 is positioned opposite a second channel 512. Channels 510 and 512 have channel outlets 514 and 516, respectively. In channel 510 is housed liquid 518. In FIG. 5B, a small droplet 520 of liquid 518 is discharged into the gap 522 between channel outlets 514 and 516. Movement of the liquid can be achieved with EOF, pneumatically or mechanical pumping. Micropipette 524 is used to transfer a small volume of liquid to the droplet 520 to form a reaction mixture. After the addition of the liquid to the droplet 520, the liquid 518 in channel 510 is pumped to cross the gap 522 and enter channel 512, where the droplet 520 comprising the reaction mixture is contained within channel 512. If one wishes, one could have prefilled channel 512, so that there would be a continuous column of liquid extending through the channels and the droplet 520 would be protected from any evaporation. As shown in the figure, only a small amount of evaporation can occur, due to the very limited interface between the liquid and the atmosphere in the channel. After incubating the reaction mixture, the occurrence of a reaction can be determined, where the reaction provides for a detectable signal. The determination may be made while the reaction mixture is in the channel, or the reaction mixture may be expressed and the signal read without interference from the material forming the channel. Alternatively, by moving the droplet 520 into the gap 522, all or a portion of the liquid in the gap 522 could be isolated with the pipette 524 and the reaction mixture analyzed.

Figure 6A:
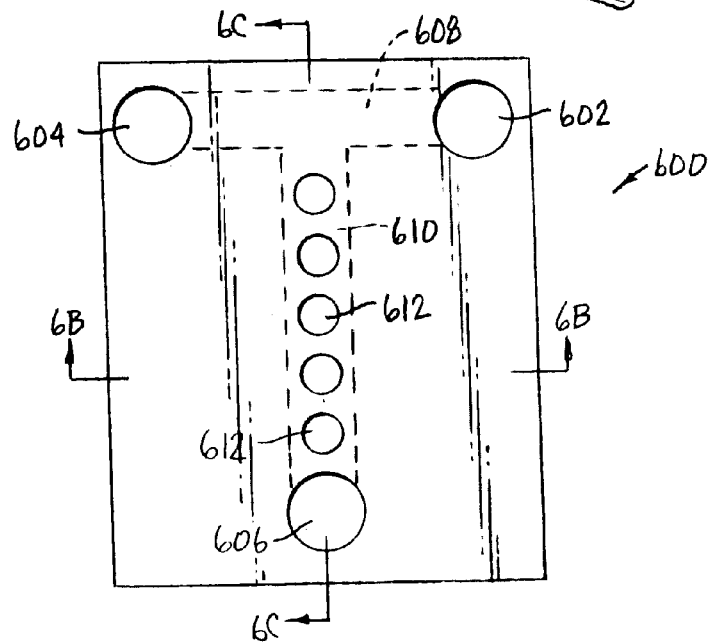
FIG. 6A is a plan diagrammatic view of a device according to this invention, with FIG. 6B a cross-sectional view along line B—B and FIG. 6C a cross-sectional view along lines C—C.
Figure 6B:
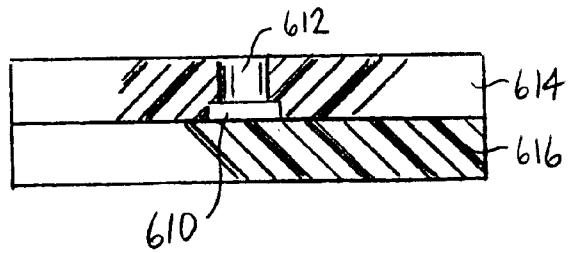
Figure 6C:
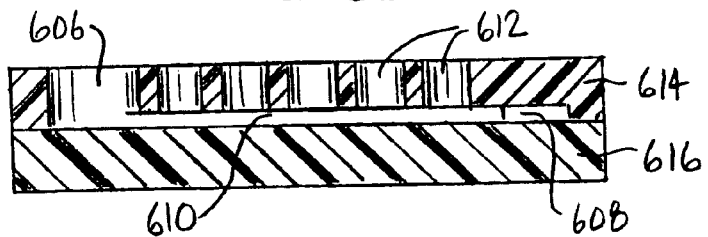

In FIGS. 6A, 6B and 6C, a device 600 is depicted with three reservoirs 602, 604 and 606, where reservoirs 602 and 604 are connected through auxiliary channel 608 and through auxiliary channel 608 to main channel 610. Reservoir 606 is at the terminus of main channel 610 opposite to the terminus of main channel 610 joined to auxiliary channel 608. Above main channel 610 are a plurality of ports 612 aligned and evenly spaced along the main channel 610, extending through the upper layer 614. Channel 610 is enclosed at its bottom by lower layer 616. While in the figure, the channel 610 is shown as having a greater width than the diameter of the port 612, this can be reversed, where the channel would have a smaller dimension than the port, and the width of the channel would control the size of the interface between the port and the channel. The effect of having a smaller channel width than the width of the port is to have a portion of the droplet in the port supported by the lower layer and out of contact with the liquid in the channel. Furthermore, smaller channels will enhance the linear velocity in the liquid for comparable levels of evaporation in the port. In using the device, an aqueous medium is introduced into the reservoirs so as to fill the channels. By having the port walls non-wettable, the aqueous medium does not rise up the walls, but forms a small convex meniscus. Solutions may be added to each of the ports and reactions performed at each port site. Preferably, there would be only one port along a channel, where there could be many main channels, each with a single port.

It should be understood that the level of the liquid in the reservoir may be the same, higher or lower than the level of the meniscus. While preferably the level will be higher, the salient consideration is that the surface tension with the wettable wall is sufficient to support the meniscus at the non-wettable/wettable interface. Therefore, as long as the liquid in the zone is at the border of the non-wettable/wettable interface and is maintained there despite evaporation from the zone, the level of the liquid in the reservoir is not critical.

Figure 7A:
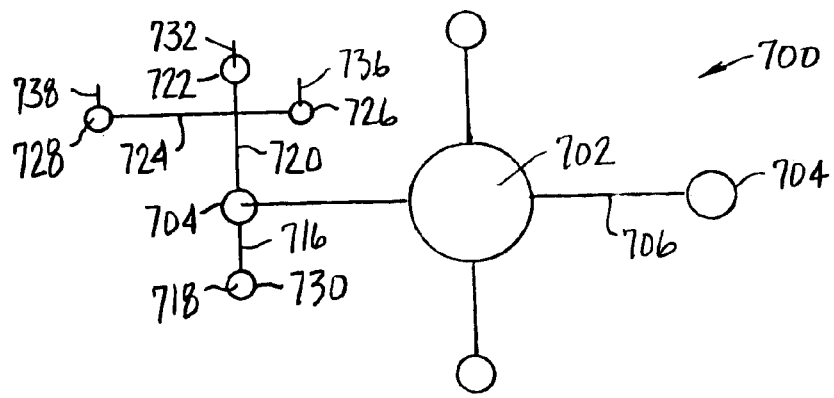
FIG. 7A is a diagrammatic plan view of a network according to this invention.
Figure 7B:
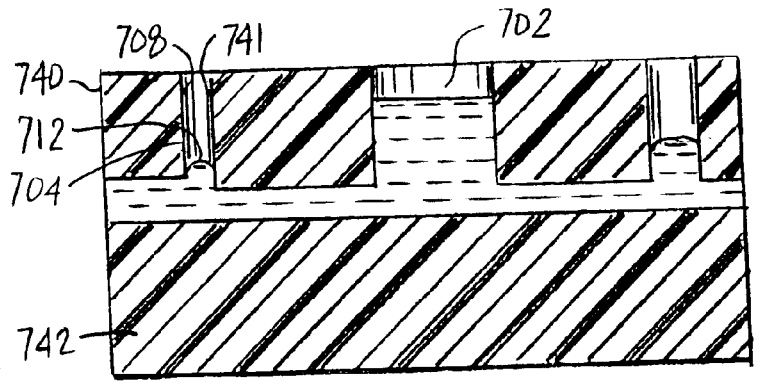
FIG. 7B is a cross-sectional view of a device corresponding to a portion of the network of FIG. 7A.

In FIGS. 7A and 7B, diagrammatic plan and cross-sectional views are depicted of a unit with electrokinesis capability for analyzing the components in the zone, while having a central distribution of reagent components from a reservoir to a plurality of zones. The unit 700 comprises a central reservoir 702, which serves to receive a solution of one or more reagents and act as a distribution center for distributing the solution to a plurality of zone enclosures 704 by means of channels 706. The solution in the central reservoir 702 is conveniently maintained at a level above the liquid level in the zone enclosure. In this situation a solution of the reagent is added to a dry central reservoir under conditions that retain the solution in the central reservoir. After adding buffer or other diluent, the solution from the central reservoir is released into the channels and to the zones. The solution migrates from the reservoir 702 through the channels 706 and enters the zone enclosure 704. Where liquid is present in the zone enclosure 704, the solution will mix with the liquid in the zone enclosure 704 to provide a reaction mixture. The zone 704 enclosure comprises an upper region 708 of the zone enclosure 704, into which the reaction mixture 710 extends, having meniscus 712, from which liquid evaporates. The zone enclosure 704 is connected by channel 716 to a buffer reservoir 718 and by channel 720 to waste reservoir 722. Thus, buffer reservoir 718, channel 716, zone closure 704, channel 720 to waste reservoir 722 define an electrokinetic channel, whereby charged components may be moved by electrophoresis and both charged and uncharged components by electroosmotic force. The channel 720 crosses channel 724, which can serve as an analytical channel. For example, it may contain a sieving polymer to separate components of different mobilities, such as proteins and protein complexes, DNA of different lengths, etc. The analytical channel 724 connects buffer reservoir 726 and waste reservoir 728. Each of the reservoirs has electrodes, where the buffer reservoir 718 has electrode 730, the complementary waste reservoir 722, electrode 732, the buffer reservoir 726, electrode 736 and the complementary waste reservoir 728, electrode 738.

The device has an upper plate 740 and a lower plate 742. The lower plate 742 has channel 744, which connects buffer reservoir 718 and waste reservoir 722 with zone enclosure 712, where the channel provides solution under the upper portion of the zone enclosure 712 with liquid from the channel 744. While the diameters and the reservoirs are shown as approximately equal in FIG. 7B, this is for illustration. In practice, the zone enclosure diameter would normally be smaller than the reservoir diameters. The non-wettable nature of the wall 741 of the zone enclosure 708 provides for a convex meniscus 712 and restricts the height to which the liquid in the zone can rise.

While not necessary to fabricate the device of two plates, the use of two plates will be of great convenience. The appropriate channels may be formed in each of the plates, independently of the other. The openings for the zones and reservoirs in the upper plate 740 may be formed to be in register with the corresponding portions of the microstructures present in the lower plate 742, while the channels in the upper plate 740 may be made independent of the microstructures in the lower plate 742. In this way a network of channels and reservoirs may be formed in the lower plate and access to these channels and reservoirs provided in the upper plate.

In carrying out an operation, the channels in the lower plate may be filled with buffer, where different buffers may be present in different channels. The buffer may contain one or more reagents and or the sample, depending upon the nature of the operation. If one wished to carry out enzyme assays, where the enzyme is an expensive reagent, one could have the enzyme provided from the central reservoir 702. One could fill the channels with buffer and enzyme substrate. The liquid from the channels will rise into the zone enclosures 704 to form a meniscus 712 and define the reaction mixture. If one is interested in the effect of a test compound on the activity of the enzyme, one could add a different test compound to each zone. One would then add the enzyme solution to the central reservoir 702, whereby the enzyme solution would move by capillary action through channels 706 to zone enclosures 704. Liquid moving from zone enclosures 704 into channels 706 may be prevented in a variety of ways, including maintaining reservoir 702 sealed until the enzyme solution is added, providing a barrier at the interface between channel 706 and central reservoir 702, which is dissolved by the solution added to central reservoir 702, and the like. Once the enzyme enters the zone enclosure 704 the enzymatic reaction will occur and product will begin to be formed. After sufficient time for product to form, the electrokinetic analysis may begin. The electrodes 730 in buffer reservoir 718 and 732 and in waste reservoir 722 are activated to begin the migration of charged species from the liquid in the zone enclosure 704 toward the waste reservoir 722. When the enzyme product reaches the intersection 746 between channel 720 and channel 724, the defined volume of product is injected into the analysis channel 724, by using electrodes 736 and 738. The product may then be separated from other components in the reaction mixture and read. Where the product is fluorescent, the product may be read with a PMT or CCD or other detection device.

In analogous manner, one could perform DNA sequencing, where the DNA sample would be put in the central reservoir, dNTPs and labeled ddNTPs in the buffer and different primers in the different zones. One would then add the polymerase to the different zones and initiate the extensions, with thermal cycling in the zones. Once the sequencing was completed, the electrophoretic analysis could begin, where the DNA fragments could be directed to the intersection 746 and the channel 724 would contain sieving buffer, to provide separation of the different length fragments.

Figure 8A:
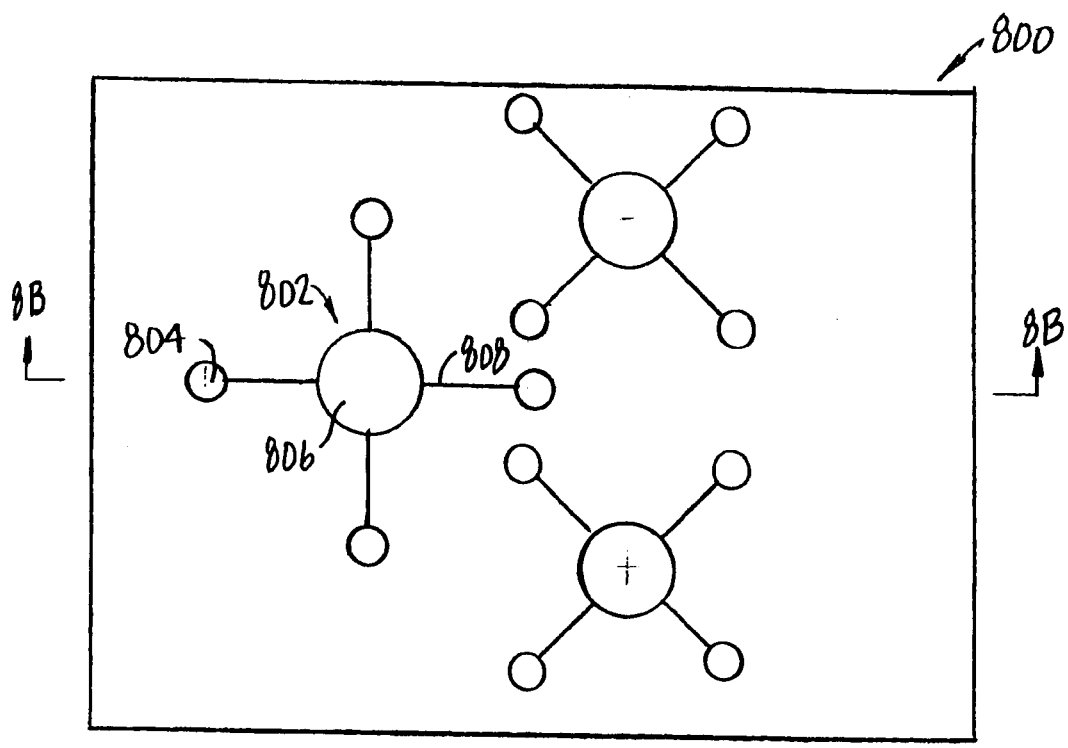
FIG. 8A is a diagrammatic plan view of a network according to this invention.
Figure 8B:
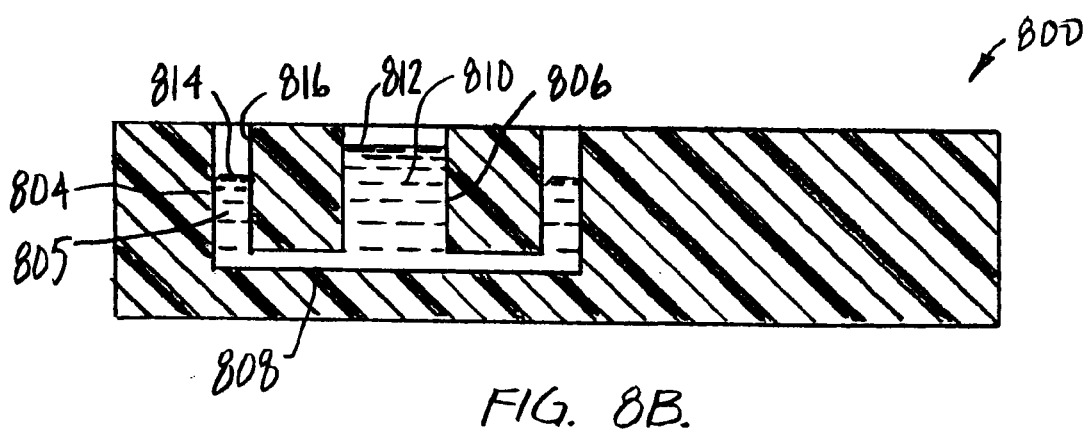
FIG. 8B is a cross-sectional view of a device corresponding to a portion of the network of FIG. 8A.

In FIG. 8 a different arrangement is provided, where the partially enclosed zone has only a single channel connection and a central reservoir for replenishing the volatile liquid in a plurality of zones. The plan view of the device 800 shows three units 802, although there would normally be many more, where the units would be distributed to provide for high density of the units 802. For clarity, each unit is shown to have only four vessels 804, although in a commercial device there would be a much greater number of vessels connected to each reservoir 806. The reservoir 806 is connected through channels 808 to the vessels 804. The reservoir 806 would normally be filled with an appropriate liquid 810 to provide liquid for replenishment of liquid evaporating from the liquid 805 in the vessels 804. The height 812 of the liquid in the reservoir 810 would provide a hydrostatic head, which would be insufficient to drive the meniscus 814 of the liquid 805 past the non-wettable region 816 in the vessel 804. For example, if one were dealing with an aqueous medium there would be a region 816 in the vessel 804, which would be non-wettable. This would result in the aqueous medium rising in the vessel 804 to the non-wettable region 816, where a convex meniscus 814 is formed. Because of the small diameter of the vessel 804, as compared to the diameter of the reservoir 806, as well as the wettable nature of the walls of the reservoir 806, there is a larger surface area for evaporation due to the meniscus 814 in the vessel 804. The surface tension of the meniscus 814 prevents the liquid in the vessel 804 from rising beyond the wettable portion of the wall of the vessel 804. The result is that as the liquid 805 in the vessel 804 evaporates, liquid from the reservoir 806 will replenish the liquid 805, so as to substantially maintain the volume of the liquid in the vessel 804. Furthermore, the movement of the liquid in the channel 808 is in the direction toward the vessel 804, so as to diminish diffusion of solutes in the liquid 805 toward the channel 808.

In carrying out operations in the liquid 805, one can have very small reaction volumes, which are maintained during the course of the reaction, regardless of whether the vessel 804 is covered or uncovered. Furthermore, during additions of solutes, where the vessel is open to the atmosphere, the inevitable evaporation of a volatile solvent is compensated by-liquid from the channel, so as to maintain the volume of liquid 805 substantially constant.

Figure 9:
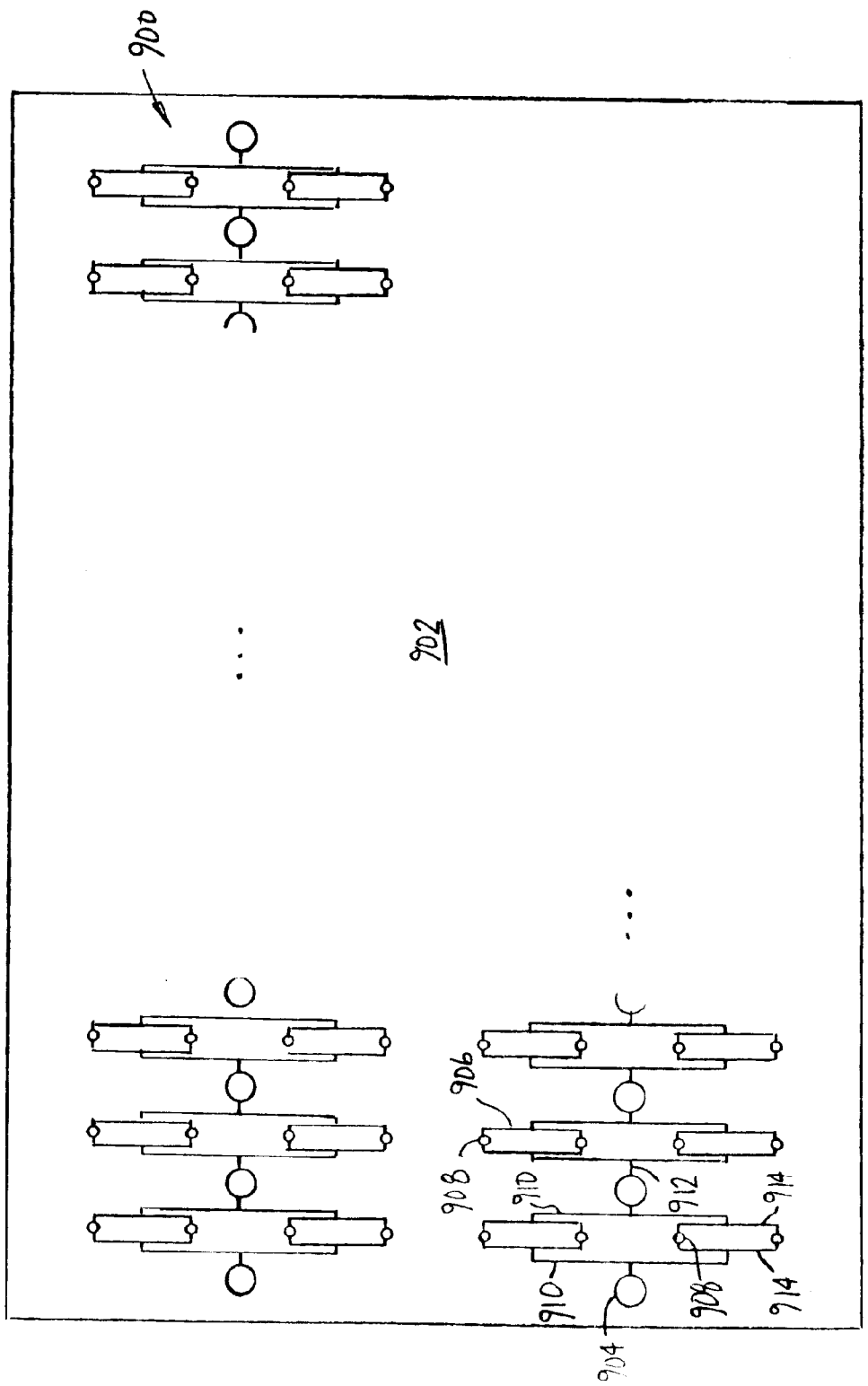
FIG. 9 is a diagrammatic plan view of an assembly of device units according to this invention having common channels along a row of device units.

In FIG. 9 is shown a diagrammatic array of a plurality of units having common channels and reservoirs in a row. The device 900 is designed to have the same distribution of zones as for a 906 well microtiter plate. The plate 902 has reservoirs 904 positioned between units 906. Each unit 906 comprises zone chambers 908 and parallel distribution channels 910, which channels are fed by reservoir connecting channels 912. Feeding channels 914 connect the distribution channels to the zone chambers 908. One would carry out determinations by filling all of the channels with the appropriate liquid buffer, where meniscuses would form in the zone chambers 908. One could fit the device to a microtiter well plate, so that the wells are in register with the zone chambers 908. By pressurizing the wells, liquid in the wells would be driven into the zone chambers 908 and mix with the liquid in the meniscus in each of the zone chambers 908. The reaction mixtures may then be incubated and the results determined by interrogating each of the zone chambers 908.

The following examples are offered by way of illustration and not by way of limitation.

EXPERIMENTAL

The following experiments were performed using a device substantially as depicted in FIG. 6. While the format of the device was kept constant, in different experiments the dimensions of the elements of the device were modified.

The device is comprised of a lower and upper plate. In the upper plate is a main channel, which forms a T at one end with an ancillary channel, which terminates in a reservoir at each end. The other end of the main channel terminates in a reservoir. Along the main channel are five evenly spaced ports formed in the upper plate. The upper plate also has openings for each of the reservoirs. The channels and reservoirs are enclosed by a base or lower plate.

The upper plate is about 1 mm in height and the lower plate is also about 1 mm in height. The port for introducing solutions is 1 mm in diameter and about 900 to 950 $\mu$m in height, while the channel provides the remaining length of the upper sheet. The channel was varied from about 0.2 mm to 3.0 mm in width, where the interface between the port and the channel varied, with either the port or the channel determining the area of interface. The reservoirs have a diameter of about 2 mm. The channels were treated with 2N sodium hydroxide for 5 mins. using a vacuum pump to ensure that the basic solution extends through the channels and reservoirs. The ports appear to be unaffected by this treatment, so that the channels and reservoirs have a hydrophilic surface, while the ports have a hydrophobic surface. One or more of the ports are used in each of the studies. Common to each of the experiments is to fill the device with 10 $\mu$l of 25 $\mu$M fluorescein diphosphate in 50 mM Tris buffer (pH 10.0) added to each of the inlet reservoirs, after prewetting the device.

In the first study, the channel is 1–2 mm wide and 10–30 nl of enzyme (alkaline phosphatase) is added to one of the ports and the fluorescence in the port is monitored for 60 mins. using a CCD camera. The fluorescence observed in the port increases with time, with the fluorescence primarily confined to the port area; a round fluorescent spot develops, which can be easily imaged with a CCD camera.

In the next study, the width of the channel is about 300 $\mu$m and 30 nl of 1 nM or 0.1 nM enzyme is added to a total of four ports and the fluorescence monitored with a CCD camera for 30 mins. The fluorescence is primarily confined to the ports and round fluorescent spots develop. The fluorescent signal can be easily related to the concentration of the enzyme introduced into the ports. Fluorescence is observed in the channel, which is substantially dimmer than the spots. The fluorescence in the channel may be attributed to the increased rate of flow of liquid in the channel due to its small dimension.

In the next study, a 2 mm wide channel is employed and 30 nl of 0.1 nM of enzyme was added to the ports and the increase in fluorescence at 5 min. intervals was monitored. A progressive increase in fluorescent signal is observed with the signal substantially confined to the ports. The amount of fluorescence in the channel is substantially less than in the previous experiment, which may be attributed to the slower rate of flow. This study was repeated with enzyme being added to two ports with a I1 mm wide channel and again the signal is substantially confined to the ports, with only dim fluorescence in the channel. In the next study, the effect of enzyme inhibitor was investigated. The channel was 1 mm in width. Approximately 30 nl of pyridoxal phosphate (250 $\mu$M or 25 $\mu$M) is added to the ports followed by the addition of 30 nl of 0.1 nM of enzyme and all of the ports closed to prevent evaporation. The fluorescence development is monitored with a CCD camera. Fluorescence is substantially confined to the ports and the fluorescent signal is related to the concentration of inhibitor introduced into the port. The port in which 250 $\mu$M inhibitor was added is still very faint at 30 mins., while the port with only 25 $\mu$M appears to be only moderately inhibited.

In the next series of studies a polyacrylic substrate was fabricated with side reservoirs of 2 mm diameter and wettable, a middle chamber of mm diameter and non-wettable, with the connecting channel 100 $\mu$m deep and 300–500 $\mu$m wide. The hydrophilic surface treatment was performed as follows. The middle chamber was sealed with Scotch® tape. The channel was filled with 4N NaOH through either of the two reservoirs, and flushed through the channel with vacuum aspiration. The treatment was repeated a number of times, allowing the basic solution to stand in the device for up to 0.5 h each time. The device was then rinsed with deionized water several times. Upon adding buffer to the reservoirs, the buffer would move through the channel by capillary action. The capacity of the device was 10 $\mu$l.

In carrying out the determinations, one protocol was to seal the middle chamber and fill the channel by adding buffer to one or both of the reservoirs. The level of the reservoirs was then allowed to equilibrate. The middle chamber was unsealed, while holding the device steady. A Nanoplotter® (GeSim Corp., Germany) was used to dispense the reactants into the middle chamber, dispensing from 40 to 100 nl in volume. Depending on the nature and complexity of the dispensing, the time for dispensing varied from under a minute to 10 mins.

The signal detection system employed an Argon ion laser source, Nikon microscopic system with 4× objective, CCD camera and image frame capture software Rainbow PVCR. Fluorescence was excited at its optimal absorbent wavelength and its emission was collected through the CCD camera and captured by software Rainbow PVCR. The images were then analyzed using ImagePro Plus software. The fluorescent intensity was then quantified.

The rate of diffusion from the middle chamber was studied as follows. 100 nl of 50 $\mu$M of 5-carboxyfluorescein in 30% DMSO was dispensed into the sample port (middle chamber). The reservoirs and channel were filled with 10 $\mu$l of 50 mM Tris buffer, pH 9.0. Fluorescence was excited at 480±nm and emission was at 530±20 nm, using the signal detection system described above. The fluorescent signals were recorded as a function of time. 80–90% of the original fluorescence intensity was maintained in the sample port region over 1 h. The fluorescent signal in the channel away from the sample port was found to be close to background. The loss of the fluorescein through the channel by diffusion is insignificant, as demonstrated in the following table.

|                    | Time, Min |        |      |      |      |
| ------------------ | --------- | ------ | ---- | ---- | ---- |
| Distance from port | 0         | 5      | 15   | 30   | 60   |
| A__340 $\mu$M      | 1         | 1.0399 | 1.03 | 1.04 | 0.86 |
| B__450 $\mu$M      | 1         | 0.94   | 1.02 | 1.07 | 0.97 |
| D__1600 $\mu$M     | 1         | 0.966  | 0.98 | 0.93 | 0.83 |

In the next study, enzyme kinetics were performed using alkaline phosphatase and substrate providing a fluorescent product. The channel was rinsed with AutoPhos buffer (JBL Scientific, Inc., San Luis Obispo, Calif.) and then filled with 10 $\mu$l of 1 mM AutoPhos substrate. 50 nl of alkaline phosphatase, at different concentrations was then dispensed into the sample port. The concentrations varied from 31.25 attomoles to 62.5 femtomoles with 2-fold dilutions. The fluorescent signals were recorded at different time points as described above. The following table indicates the results.

| ENZYME KINETIC ASSAY RESULTS | | | | | |
| --- | --- | --- | --- | --- | --- |
| | Conc., nM | | | | |
| Time | 1000 | 250 | 125 | 31.25 | 0 |
| 12 min. | 13390.8 | 2913.84 | 1497.68 | 821.08 | 0 |
| 20 min. | 20692.4 | 4698.56 | 2323.8 | 1055.88 | 0 |
| 30 min. | 28981.6 | 7579 | 2892.68 | 1798.84 | 0 |

As evidenced by the above results, the rate of the reaction is linear with the enzyme concentration in accordance with a 1st order reaction.

The next study evaluated the system using a competitive inhibition assay, 4-Nitrophenyl phosphate (PNPP) (Sigma Chemical Co., St. Louis, Mo.) was used as a non-fluorescent substrate for alkaline phosphatase (20 femtomoles) competing with the AutoPhos substrate. The channel was rinsed with AutoPhos buffer and filled with 1 mM AutoPhos substrate. Into the sample port was introduced 100 nl of PNPP at concentrations varying from 0 to 10 mM and the fluorescent signal was determined at different reaction time points. The fluorescent signal was found to diminish with increasing inhibitor concentration, the following table providing the results.

| ENZYME INHIBITION ASSAY | | | | | | | | | | |
|---|---|---|---|---|---|---|---|---|---|---|
| Inhibitor conc., mM | 0.001 | 0.0025 | 0.005 | 0.01 | 0.02 | 0.3125 | 0.625 | 1.25 | 5 | 10 |
| Fluorescent Signal x103 | 4.5 | 4.0 | 4.0 | 3.5 | 2.6 | 2.0 | 1.6 | 1.6 | 1.6 | 1.5 |

In another series of studies binding assays were performed using fluorescence resonance energy transfer. The procedure employed is as follows. The channel was rinsed and filled with 25 μl of rhodarnine labeled streptavidin and 100 nl of fluorescein labeled biotin dispensed in the sample port. The concentration of the antigen varied from 0 to 100 μM by 2-fold dilutions. The signal detection system was as described, except that emission was detected at 600±20 nm. The energy transfer increased corresponding to the increase in antigen. The study was repeated varying the amount of labeled streptavidin while keeping the ibotin-fluorescein at 25 μM. The background FRET signal contributed by rhodamine-streptavidin alone was substantially negligible, when the concentration of rhodamine-streptavidin was greater than about 2 μM. The following tables provide the results for the two studies.

| BINDING ANTIGEN-RECEPTOR ASSAYS | | | | | | |
|---|---|---|---|---|---|---|
| | Conc. Of Fluorescein | | | | | |
| Labeled antigen, mM | 100 | 50 | 25 | 10 | 5 | 0 |
| FRET Signal | 2956 | 2327 | 1639 | 869 | 370 | 0 |

In the next study the channel was rinsed and filled with 25 mM fluorescein-labeled antigen, 100 nl of rhodamine-labeled receptor dispensed into the sample port. Various concentrations of the rhodamine-labeled receptor were employed, with excitation and emission as described above. The following table indicates the change in FRET signal with concentration of the rhodamine-labeled receptor. The background signal contributed by rhodamine-receptor alone is also indicated.

In the next study, the effect of inhibitor on the observed signal was investigated. Fluorescein-biotin was maintained at 50 μM and rhodamine-streptavidin at 25 μM. the signal was read at 600±20 nm at varying concentrations of biotin as a binding inhibitor, with 100 nl of the binding inhibitor being added to the sample port. The energy transfer decreased with increase of binding inhibitor.

In the next study, the channel was filled with varying concentrations of biotin in the range of 0 to 5 μM and 100 nl of 250 nM rhodamine-labeled streptavidin (625 nM) followed by 100 nl of 1.0 μM fluorescein-biotin added to the sample port. After incubating for 60 min., the signal was detected at 520±20 nm. The results are reported as fraction inhibition. The following tables provide the results.

| INHIBITION OF BINDING OF ANTIGEN-RECEPTOR ASSAYS | | | | | | | | | | |
|---|---|---|---|---|---|---|---|---|---|---|
| Conc. Of Inhibitor, nM | 0 | 0 | 30 | 60 | 180 | 240 | 500 | 600 | 1000 | 5000 |
| Fraction of Inhibition | 0 | 0.0177 | 0.0385 | 0.0310 | 0.050 | 0.0514 | 0.224 | 0.3664 | 0.950 | 1.0 |

It is evident from the above results that the subject devices and methods provide for efficient manipulations of small volumes and determinations of a wide variety of events, such as chemical reactions, binding events, enzyme reactions, and the like. The subject invention has great flexibility in the variety of protocols, which may be employed, with a single device allowing for different protocols. In addition, the subject devices may be combined with other devices, such as microtiter well plates, where the subject device may be in registry with the wells, so that samples may be readily followed and results recorded with confidence as to the compound involved.

Each reference cited herein is incorporated by reference as if the reference was set forth verbatim in the text of this specification.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

| Labeled receptor, mM | 0 | 0.25 | 0.5 | 1.5 | 3.5 | 5 | 6 | 8 | 12 |
|---|---|---|---|---|---|---|---|---|---|
| FRET Signal | | 2192 | 3663 | 2264 | 3254 | 7619 | 10604 | 10882 | 11952 | 11552 |
| Background Signal | | 1923 | 1430 | 2336 | 1312 | 556 | 211 | 516 | 759 | 1005 |

What is claimed is:

1. A microfluidic device comprising (a) a solid substrate,
(b) formed in the substrate, a channel network having (i) one or more reservoirs, and (ii) one or more capillary channels connecting the reservoirs in fluid communication with one another, said network having wall portions that are sufficiently wettable to promote flow of a liquid in the network by capillarity along such wall portions, and
(c) formed on at least one of said wall portions, a non-wettable region effective to block liquid flow by capillarity past or through said non-wettable region.

2. A microfluidic device according to claim 1, wherein said microfluidic device comprises a central reservoir connected to at least two capillary channels.

3. The microfluidic device of claim 1 wherein at least one of said reservoirs is a zone for receiving sample material in a sample assay.

4. The microfluidic device of claim 3 wherein at least one of the reservoirs is in fluid communication with said zone reservoir for supplying liquid to the zone through a capillary channel.

5. The microfluidic device according to claim 1, further comprising means for applying a force to the liquid to move the liquid past the non-wettable region.

6. The microfluidic device according to claim 5, wherein the applying means includes at least one pair of electrodes placed across a region of said wall portions, and a voltage source connected to the electrodes for inducing electroosmotic flow.

* * * * *